(12) United States Patent
Kearns et al.

(10) Patent No.: US 11,931,415 B2
(45) Date of Patent: Mar. 19, 2024

(54) OPHTHALMIC COMPOSITIONS

(71) Applicant: The University of Liverpool, Liverpool-Merseyside (GB)

(72) Inventors: Victoria Kearns, Liverpool-Merseyside (GB); Helen Cauldbeck, Liverpool-Merseyside (GB); Steve Rannard, Liverpool-Merseyside (GB); Rachel Williams, Liverpool-Merseyside (GB); Maude Le Hellaye, Saint Justin (FR)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 128 days.

(21) Appl. No.: 16/324,298

(22) PCT Filed: Aug. 9, 2017

(86) PCT No.: PCT/GB2017/052356
§ 371 (c)(1),
(2) Date: Feb. 8, 2019

(87) PCT Pub. No.: WO2018/029477
PCT Pub. Date: Feb. 15, 2018

(65) Prior Publication Data
US 2019/0175742 A1 Jun. 13, 2019

(30) Foreign Application Priority Data
Aug. 9, 2016 (GB) ..................................... 1613696

(51) Int. Cl.
| | | |
|---|---|---|
| *A61K 47/59* | (2017.01) | |
| *A61K 9/00* | (2006.01) | |
| *A61K 31/192* | (2006.01) | |
| *A61K 31/203* | (2006.01) | |
| *A61K 45/06* | (2006.01) | |
| *A61K 47/34* | (2017.01) | |
| *A61P 27/02* | (2006.01) | |

(52) U.S. Cl.
CPC ............ *A61K 47/59* (2017.08); *A61K 9/0048* (2013.01); *A61K 31/192* (2013.01); *A61K 31/203* (2013.01); *A61K 45/06* (2013.01); *A61K 47/34* (2013.01); *A61P 27/02* (2018.01)

(58) Field of Classification Search
CPC ......... A61P 27/02; A61K 45/06; A61K 47/59; A61K 9/0048; A61K 47/34; A61K 31/192; A61K 31/203
See application file for complete search history.

(56) References Cited

U.S. PATENT DOCUMENTS

| | | | | |
|---|---|---|---|---|
| 5,955,109 A * | 9/1999 | Won | ....................... | A61K 8/671 424/501 |
| 8,608,632 B1 * | 12/2013 | Brigatti | ................ | A61N 5/1017 600/7 |
| 2003/0022831 A1 | 1/2003 | Rothbard et al. | | |
| 2004/0234609 A1 * | 11/2004 | Collier | ................... | C07K 14/21 424/488 |
| 2009/0074685 A1 * | 3/2009 | Lai | ........................... | A61K 8/37 424/59 |
| 2010/0323023 A1 | 12/2010 | Garvey et al. | | |
| 2013/0281637 A1 | 10/2013 | Ueno et al. | | |
| 2014/0350101 A1 * | 11/2014 | Arvidsson | .............. | A61K 31/22 514/511 |
| 2014/0357729 A1 * | 12/2014 | Horisawa | ................ | A61P 17/00 514/772.3 |

FOREIGN PATENT DOCUMENTS

| | | | | |
|---|---|---|---|---|
| JP | 06145045 A | * | 7/1994 | |
| WO | WO-9219233 A2 | * | 11/1992 | ............. A61K 47/34 |
| WO | WO-2005028539 A2 | * | 3/2005 | ......... A61K 31/4709 |
| WO | 2006122973 A1 | | 11/2006 | |
| WO | WO-2011140101 A1 | * | 11/2011 | ............ C07F 7/0849 |
| WO | WO-2013138346 A1 | * | 9/2013 | ............. A61K 47/59 |
| WO | 2016102663 A1 | | 6/2016 | |
| WO | 2016210087 A1 | | 12/2016 | |

OTHER PUBLICATIONS

Huhtala et al., The Effects of 5-Fluorouracil on Ocular Tissues In Vitro and In Vivo after Controlled Release from a Multifunctional Implant, Investigative Ophthalmology & Visual Science May 2009, vol. 50, 2216-2223.*
Songhan Plastic Technology, Dow Corning ST Cyclomethicone 5-NF, printed from http://www.lookpolymers.com/polymer_Dow-Corning-ST-Cyclomethicone-5-NF.php, Dec. 7, 2021, 3 pages.*
Dupont, LiveoTM ST-Elastomer 10, printed from https://dupont.materialdatacenter.com/en/products/datasheet/SI/Liveo%E2%84%A2%20ST-Elastomer%2010, Dec. 7, 2021, 4 pages.*
Personal Care Magazine, Selecting the perfect silicone for your formulation, Jul. 9, 2014, printed from https://www.personalcaremagazine.com/story/13149/selecting-the-perfect-silicone-for-your-formulation, 5 pages.*
ABC Science, Vitamins: how do they work?, Oct. 13, 2010, printed from https://www.abc.net.au/science/articles/2010/10/13/3037285.htm, 3 pages.*

(Continued)

*Primary Examiner* — Sean M Basquill
(74) *Attorney, Agent, or Firm* — FOX ROTHSCHILD LLP

(57) ABSTRACT

A composition comprises: a base oil; an additive; and a drug. The additive has segments which are conjugated, e.g. covalently linked, together. A first segment facilitates solubility in the base oil, whereas a second segment facilitates drug solubility and/or modifies drug release or other behaviour. The first segment may for example comprise a poly(dimethylsiloxane)-containing moiety. The second segment may for example resemble a drug molecule. The composition may for example be used as a tamponade or as a component for a tamponade administered to the eye.

17 Claims, 7 Drawing Sheets

(56) References Cited

OTHER PUBLICATIONS

Siddikuzzaman and V.M. Berlin Grace, Antioxidant Potential of All-trans Retinoic Acid (ATRA) and Enhanced Activity of Liposome Encapsulated ATRA Against Inflammation and Tumor-Directed Angiogenesis, 35 Immunopharmacol. Immunnotoxicol. 164 (Year: 2013).*

* cited by examiner

OPHTHALMIC COMPOSITIONS

The present invention is directed towards ophthalmic compositions and components thereof. The compositions may be administered into the eye, for example within the vitreous space of the eye, for therapeutic purposes. They may be used as, or as part of, tamponades which have a physical effect. The compositions may be used to treat retinal detachment, and in procedures for treating retinal detachment such as vitrectomies.

The retina is a light-sensitive layer, which is from 0.1-0.32 mm thick and has an approximate diameter from 30-40 mm and lines the back of the interior of the eye. The main function of the retina is to direct an inverted image via a light signal, which is then converted into a communicable chemical signal by photo-transduction. The ordered pattern is then sent to the brain through the optic nerve. The centre of the retina is the only part capable of fine detailed vision.

The structure of the retina can be divided into two layers: the inner neuroretina and the outer epithelial monolayer consisting of retinal pigment epithelium, which is a layer of hexagonally close packed cells situated at the back of the human eye. The neuroretina contains photoreceptors and the retinal pigment epithelium forms an outer layer on the Bruch's membrane. The retinal pigment epithelium has several functions namely, light absorption, epithelial transport, spatial ion buffering, visual cycle, phagocytosis, secretion and immune modulation. In particular, the retinal pigment epithelium provides nutrients to the inner visual cells, as well as transporting metabolic waste to the choroid.

Retinal detachment occurs when the inner neuroretina becomes detached from the supporting retinal pigment epithelium. There are several causative factors that can result in retinal detachment, such as a traumatic event, diabetic proliferative retinopathy and cataract surgery. If the retina remains detached, it will degenerate and lose its ability to function. Thus, failure to treat retinal detachment quickly and effectively can lead to permanent localised loss of vision (e.g. central vision will be lost if the macular remains detached) or permanent loss of vision.

There are different types of retinal detachment: i) rhegmatogenous retinal detachment, which is caused by a tear or break in the retina and the accumulation of vitreous humour between the detached retina and the retinal pigment epithelium that can cause further separation between the two layers; ii) exudative retinal detachment, which is caused by a build-up of fluid from blood vessels behind the retina that may be triggered by conditions such as severe macular degeneration, very high blood pressure, and certain cancers, such as choroidal melanoma; and iii) tractional retinal detachment, which is caused by pulling on the retina that can occur as a result of, or a complication of, other conditions, such as diabetic proliferative retinopathy and proliferative vitreoretinopathy.

Proliferative vitreoretinopathy is a condition that can follow a break in the retina where a scar-like membrane formation occurs, analogous to dynamic wound healing. The scar-like tissue then creates traction that pulls the neuroretina from the supporting retinal pigment epithelium, which leads to tractional retinal detachment.

Traumatic proliferative vitreoretinopathy occurs at the vitreoretinal interface and it results from a perforating trauma to the posterior segment of the eye, or it can happen following surgical intervention. Proliferative vitreoretinopathy is a complication that follows rhegmatogenous retinal detachment, especially if there has been a severe retinal tear. Proliferative vitreoretinopathy occurs in approximately 5-10% of all rhegmatogenous retinal detachments, and proliferative vitreoretinopathy is also implicated in re-detachment after surgery in 75% of cases, making proliferative vitreoretinopathy the most common cause of failure of rhegmatogenous retinal detachment surgery.

During trauma or rhegmatogenous retinal detachment, the retinal pigment epithelium loses contact with adjacent cells, and consequently loses cellular signalling. The retinal pigment epithelium then comes into contact with different growth factors and cytokines, triggering the cells to proliferate, de-differentiate and migrate to repair the defect. The retinal pigment epithelium cells undergo epithelial-mesenchymal transition where the microvilli retract causing a loss of adhesion to the neuroretina and their extracellular matrix. The cells then round up and detach from their basement membrane. Retinal pigment epithelium cells then de-differentiate into wound repair phenotypes, similar to fibroblasts and macrophages which construct a membrane, as they migrate towards the vitreous space. This differentiation is regulated by various growth factors (platelet-derived growth factor, TGF-β, epidermal growth factor, tumour necrosis factor alpha, FGF and others) as well as cytokines (interleukin 1, 6, 8, 10 and interferon-gamma). Retinal pigment epithelium cells are the main component of the membranes. However, other cells involved include fibroblasts, which are responsible for tissue repair, in particular scar formation, myofibroblasts and macrophages, as well as minor amounts of glial cells. The resulting membranes contract and distort/pull on the retina leading to tractional retinal detachment.

There are numerous ways in which retinal detachment can be treated, which all have the underlying aim of reattaching the retina to the retinal pigment epithelium and fixing any tears or breaks that may be present in the retina. One such treatment is vitrectomy followed by the insertion of a tamponade, which fills the vitreous space.

A vitrectomy is the surgical removal of the vitreous liquid from the eye, which involves the removal of the vitreous liquid through small cuts in the sclera. The vitreous liquid is then replaced by saline, which itself can be subsequently replaced by air, gas or a silicone oil tamponade. The tamponade prevents access of any remaining aqueous components to the site of the tear, which inhibits migration of any aqueous components into the sub-retinal space, excluding any inflammatory factors and initiating retinal detachment.

Air and gas are temporary tamponades that last anywhere from days (e.g. in the case of air) to weeks, depending on the gas used (e.g. perfluorocarbon gases have a residency of two-three weeks). However, during the use of air or gas tamponades, the patient should lie predominantly facing downwards for a period of 4 weeks to ensure that the air or gas bubble is aligned with the damaged region and any remaining vitreous material is held away from the repair site as the motion of the viscous fluid may lead to greater damage. Silicone oils and derivatives thereof, on the other hand, are the only class of long term tamponades whose effects do not dissipate over time. It is, however, necessary to remove the silicone oil after the initial surgery (e.g. two to eight months after the initial surgery).

Alternatives to silicone oils have been investigated. One such alternative is fluorinated silicone oil. The specific gravity of fluorinated silicone oil can be tailored depending on the ratio of fluorinated silicone oil to silicone oil, but the low viscosity of fluorinated silicone oil can cause a macrophagic response. It is also not automatically safe to use highly viscous fluorinated silicone oil as white deposits on the retina have been observed with materials of 1750 mPa·s.

Other additives to silicone oil have been investigated, such as semi-fluorinated alkanes, which are transparent and immiscible with water. Semi-fluorinated alkanes act as an amphiphilic surfactant as the hydrocarbon end is highly hydrophobic whereas the fluorocarbon end is less hydrophobic. The specific gravity of semi-fluorinated alkanes can be determined by the length of the alkane chain. The use of semi-fluorinated alkanes in a clinical environment as the sole tamponade agent has been restricted because of dispersion effects, which can induce a macrophagic response. Accordingly, studies using mixtures of semi-fluorinated alkanes with silicone oils have been undertaken. In those studies, the solubility of the semi-fluorinated alkanes was found to be determined by the viscosity of the silicone oil and the molecular weight of the semi-fluorinated alkanes, and increasing either will reduce the solubility of the semi-fluorinated alkanes.

It has been found that additional treatments are required in certain circumstances. For example, when treating proliferative vitreoretinopathy, corticosteroids may be administered intravitreally to combat the inflammatory response caused by a break or tear in the retina. However, corticosteroids can also be applied topically, subconjunctival injections and, less frequently, sub-tenon injections, orbital floor injections or retrobulbar injections. The tensional forces can be relieved by surgery, which removes scar tissue that has formed and is referred to as membrane pealing. A vitrectomy is usually performed at the same time as the membrane peeling.

In the event that retinal reattachment is not achieved quickly and effectively, there remains no effective preventative treatment for proliferative vitreoretinopathy. This may be attributable to the difficulty in achieving therapeutic drug levels in the vitreous space and retina through conventional routes of administration. It is possible to administer drugs intravitreally or subconjunctivally, but proliferative vitreoretinopathy is a long term condition that requires treatment over a period of several weeks and the half-life of most drugs in the vitreous space or subconjunctival cavity is short. Further, repeated injections can cause complications, such as infections, inflammation and elevated intraocular pressure and/or a build-up of drug to toxic levels.

To date, various pharmacological agents have been investigated to reduce and/or prevent proliferative vitreoretinopathy. The two main categories are anti-inflammatory and anti-proliferative drugs, but studies have also been performed with antioxidants, antineoplastic and antigrowth factors, alone and as combination therapies of two or more drugs. There has not, however, been a satisfactory way in which to administer drugs. The existing drug delivery devices suffer from a multitude of drawbacks, such as limitations in drug content and release amounts (in the case of contact lenses), release of the drugs too quickly or too soon (in the case of liposomes and inserts), difficulty to reverse in the event of adverse effects (in the case of micro- and nano-particles), and the potential to cause infections (in the case of explants, such as scleral buckles).

There therefore remains a need for a new and improved composition that can be used to treat eye disorders, which does not suffer from the drawbacks of the prior art and existing approaches. Specifically, there remains a need for a composition that can be used to prevent or treat disorders, such as proliferative vitreoretinopathy, and effectively deliver drugs over a prolonged period. Advantageously, the amounts delivered over a prolonged period of time are also non-toxic. It has been found that the composition of the present invention, which comprises a base oil, a conjugated additive and a drug, achieves the desired effects of safely and effectively delivering drugs over a prolonged period.

Thus, according to a first aspect of the present invention, there is provided a composition comprising:
a base oil;
a conjugated base oil additive; and
a drug.

The present invention is particularly advantageous because the components that are used are intended to be non-toxic. The compositions are also advantageous because they have an advantageous effect in solubilising and releasing drugs in addition to a physical filling effect.

Thus the composition may be an ophthalmic composition, e.g. a composition suitable for application into the eye or suitable for application to a tamponade, or an ophthalmic tamponade itself.

In one arrangement, any suitable base oil may be used, such as a silicone oil, a fluorinated silicone oil or a perfluorocarbon oil. The base oil may comprise one or more silicone oils, fluorinated silicone oils, perfluorocarbon oils, or mixtures thereof. Alternatively, the base oil may comprise exclusively silicone oil, fluorinated silicone oil or perfluorocarbon oil. The silicone oil may be poly(dimethylsiloxane). In one arrangement, the base oil may comprise purified polydimethylsiloxane, such as $SiO_{1000}$, $SiO_{5000}$ or the commercial products Siluron® 2000, Siluron® 5000 and Siluron® 1000, which are obtained from Fluron® GmBH of Magirus-Deutz-Straβ 10, 89077 Ulm, Germany, or the commercial products Sil-1000® and Sil-5000®, which are obtained from D.O.R.C. Dutch Ophthalmic Research Center (International) B.V. of P.O. Box 43, 3214 ZG Zuidland, The Netherlands, or the commercial products Oxane 1300 and Oxane 5700, which are obtained from Bausch+Lomb, 106 London Road, Kingston upon Thames, Surrey, KT2 6TN, England, or mixtures thereof. In another arrangement, the base oil may comprise a high-density silicone oil that comprises polydimethylsiloxane and perfluorohexyloctane, such as the commercial products Densiron® 68, Densiron® Xtra and Siluron® Xtra. It will be understood that other equivalent commercial products could be used that achieve a similar technical effect.

The kinematic viscosity of different types of base oils, such as polydimethylsiloxane base oils or a high-density silicone oils that comprise polydimethylsiloxane and perfluorohexyloctane, is expressed in centistokes (1 cSt=$10^{-6}$ $m^2$/s), and arises from both the molecular weight and the length of the polymer; increasing SiO molecular weight results in an increased polymer chain length and consequently an increased viscosity. In one arrangement, the kinematic viscosity of the base oil may range from about 100 to about 10,000 cSt, form about 200 to about 9,500 cSt, from about 300 to about 9,000 cSt, from about 400 to about 8,500 cSt, from about 500 to about 8,000 cSt, from about 600 to about 8,500 cSt, from about 700 to about 7,000 cSt, from about 800 to about 6,500 cSt, from about 900 to about 6,000 cSt, from about 950 to about 5,500 cSt, from about 1,000 to about 5,000 cSt, from about 1,100 to about 4,900 cSt, from about 1,200 to about 4,800 cSt, from about 1,300 to about 4,700 cSt, from about 1,400 to about 4,600 cSt, from about 1,500 to about 4,500 cSt, from about 1,700 to about 4,300 cSt, from about 1,900 to about 4,100 cSt, from about 2,000 to about 4,000 cSt, from about 2,200 to about 3,800 cSt, from about 2,400 to about 3,600 cSt, from about 2,600 to about 3,400 cSt, or from about 2,800 to about 3,200 cSt. In another arrangement, the kinematic viscosity of the base oil may be about 500 cSt, about 600 cSt, about 700 cSt, about 800 cSt, about 900 cSt, about 1,000 cSt, about 1,100 cSt, about 1,200 cSt, about 1,300 cSt, about 1,400 cSt, about 1,500 cSt, about 1,700 cSt, about 1,900 cSt, about 2,100 cSt, about 2,300 cSt, about 2,500 cSt, about 2,700 cSt, about 2,900 cSt, about 3,100 cSt, about 3,300 cSt, about 3,500 cSt, about 3,700 cSt, about 3,900 cSt, about 4,100 cSt, about 4,300 cSt, about 4,500 cSt, about 5,000 cSt, about 6,000 cSt, about 7,000 cSt, about 8,000 cSt, about 9,000 cSt, about 10,000 cSt.

The term "conjugated base oil additive" herein denotes an additive which has segments which are conjugated, i.e. linked, e.g. covalently linked, together. A first segment facilitates solubility in the base oil, whereas a second segment facilitates drug solubility and/or modifies drug release or other behaviour.

In other words, the additive may comprise at least one base oil—compatible segment or moiety, and at least one drug—compatible segment or moiety.

Optionally, the additive may also be "conjugated" in a different sense of the word, i.e. may contain alternating saturated and unsaturated bonds, for example within the second segment (e.g. to be similar to such conjugation in certain drugs, for a "like dissolves like" effect), but such conjugation is optional rather than essential.

The use of a conjugated base oil additives with segments similar to the base oil is particularly advantageous because it reduces solubility issues. In the absence of a conjugated additive, the free drug would need to be released solely by diffusion through the oil, which has been found to happen in an uncontrolled manner over the period of a week in vivo in a rabbit model based study.

In one arrangement, the base oil part of the additive may be conjugated to a hydrophobic moiety. Any suitable hydrophobic moiety may be used, such that it may be non-toxic and/or oil soluble and/or prevents proliferation. In one arrangement, the hydrophobic moiety may be non-toxic. In another arrangement, the hydrophobic moiety may be soluble in the base oil. In a further arrangement, the hydrophobic moiety may prevent proliferation in the event that it is cleaved from the base oil part of the additive, such as the poly(dimethylsiloxane) part of the additive.

In one arrangement, the hydrophobic moiety may be selected from optionally substituted $C_{1-25}$ alkyl groups, optionally substituted $C_{2-25}$ alkenyl groups, optionally substituted $C_{7-25}$ alkyl-aryl groups, or optionally substituted $C_{8-25}$ alkenyl-aryl groups, optionally substituted $C_{1-10}$ alkyl-O-$C_{1-10}$ alkyl groups, optionally substituted amine groups (—NRR', where R and R' are independently selected from H, OH, a $C_{1-10}$ alkyl group, a $C_{2-10}$ alkenyl group, a $C_{7-25}$ alkyl-aryl group, or a $C_{8-25}$ alkenyl-aryl group), optionally substituted amide groups (—C(=O)NRR', where R and R' are independently selected from H, a $C_{1-10}$ alkyl group, a $C_{2-10}$ alkenyl group, a $C_{7-25}$ alkyl-aryl group, or a $C_{8-25}$ alkenyl-aryl group), or optionally substituted ester groups (—COOR, where R is selected from a $C_{1-10}$ alkyl group, a $C_{2-10}$ alkenyl group, a $C_{7-25}$ alkyl-aryl group, or a $C_{8-25}$ alkenyl-aryl group). In another arrangement, the hydrophobic moiety may be selected from optionally substituted $C_{1-25}$ alkyl groups, optionally substituted $C_{2-25}$ alkenyl groups, optionally substituted $C_{7-25}$ alkyl-aryl groups, or optionally substituted $C_{8-25}$ alkenyl-aryl groups.

In a further arrangement, the hydrophobic moiety may have a positive drug action, be a drug and/or resemble a drug that may be used in the eye, e.g. in the treatment of eye disorders.

In one arrangement, the hydrophobic moiety may be a drug. Any suitable drug may be used. The drug may be present as the free drug, for example in neutral, acidic or basic form. The drug may be an anti-inflammatory drug, an anti-proliferative drug, an anti-growth factor drug, such as anti-VEGF (anti-vascular endothelial growth factor) antibody, for example ranibizumab and bevacizumab, and other suitable drugs, for example aflibercept, an anti-oxidant drug, an anti-neoplastic drug or mixtures thereof. In one arrangement, the drug may be selected from an anti-inflammatory drug, an anti-proliferative, an anti-oxidant drug, or mixtures thereof. In another arrangement, the drug may be selected from anti-proliferative drugs, such as all-trans retinoic acid, or anti-inflammatories, such as non-steroidal anti-inflammatories, e.g. ibuprofen. In one arrangement, the drug may be all-trans retinoic acid. In an alternative arrangement, the drug may be ibuprofen.

Retinoic acid is particularly advantageous when used in the present invention because it has anti-proliferative and anti-oxidant effects and it is known to reduce proliferative vitreoretinopathy and retinal pigment epithelium cell proliferation, as well as being used to treat leukaemia and acne. Retinoic acid is a derivative of vitamin A, which is already present in the eye and plays a role in the visual cycle and so its use is particularly advantageous. Retinoic acid also is less aggressive than some other anti-proliferative drugs, such as 5-fluorouracil, and it is soluble in silicone oil. All-trans retinoic acid is not just an antiproliferative but has a range of other effects including anti-inflammatory activity. Ibuprofen is particularly advantageous because it is a non-steroidal anti-inflammatory drug that is widely used for pain relief. Ibuprofen is soluble in silicone oil.

In one arrangement, the hydrophobic moiety may be structurally similar to, or a derivative of, anti-proliferative drugs/agents, anti-growth factor drugs/agents, such as anti-VEGF (anti-vascular endothelial growth factor) antibodies, for example ranibizumab and bevacizumab, and other suitable drugs/agents, for example aflibercept, anti-oxidant drugs/agents, anti-neoplastic drugs/agents or mixtures thereof. For example, the anti-proliferative agents may be derivatives of vitamin A, such as derivatives of all-trans retinoic acid, and the anti-inflammatory agents may be derivatives of non-steroidal anti-inflammatory agents, such as derivatives of ibuprofen.

In an alternative arrangement, the hydrophobic moiety may be a drug. Any suitable drug may be used. The drug may be an anti-proliferative agent or an anti-inflammatory agent.

For example, the anti-proliferative agent may be a derivative of vitamin A, such as all-trans retinoic acid, and the anti-inflammatory agent may be a non-steroidal anti-inflammatory agent, such as ibuprofen, or a derivative thereof.

In one arrangement, the conjugated base oil additive may comprise any suitable base oil, such as a silicone oil, a fluorinated silicone oil or a perfluorocarbon oil. The conjugated base oil additive may comprise one or more silicone oils, fluorinated silicone oils, perfluorocarbon oils, or mixtures thereof. Alternatively, the conjugated additive may comprise exclusively silicone oil, fluorinated silicone oil or perfluorocarbon oil. In one arrangement, the conjugated additive may be a conjugated poly(dimethylsiloxane) additive.

In one arrangement, the base oil part of the additive, such as the poly(dimethylsiloxane) part of the additive, may terminate in one or more functional groups to facilitate conjugation to the hydrophobic moiety. The functional groups may be any suitable functional groups that facilitate conjugation to the hydrophobic moiety. In one arrangement, the functional groups may be one or two hydroxyl alkyl groups. In one arrangement, the poly(dimethylsiloxane) part of the additive may be bis(hydroxyalkyl) terminated.

The base oil part of the additive, such as the poly(dimethylsiloxane) part of the additive may be covalently linked to the hydrophobic moiety. The base oil part of the additive, such as the poly(dimethylsiloxane) part of the additive, may be covalently linked by any suitable functional group, such as an ester group, an amide group, a carbamate group, a carbonate group, an anhydride group, and imine group, or an ether group. In one arrangement, the base oil part of the additive, such as the poly(dimethylsiloxane) part of the additive, may be covalently linked to the non-toxic group by an ester group. The non-toxic group and poly(dimethylsiloxane) part of the additive may undergo an esterification reaction to form the covalent linkage, e.g. by an esterification reaction between a carboxylic acid group of the hydrophobic moiety and an alcohol group of the poly(dimethylsiloxane) part of the additive, such as an alcohol group of the terminal hydroxyl alkyl group. The esterification reaction may be a Steglich esterification reaction or it may proceed via an anhydride reaction, for example. It will be understood that other possible esterification reactions are possible.

Without wishing to be bound by theory, it is thought that interactions between the conjugated (i.e. covalently linked) group of the additive and the free drug aids solubility in the base oil and/or modifies release of the drug from the base oil. Similarly, it is thought that an analogous interaction between the poly(dimethylsiloxane) part of the additive and the base oil aids solubility. Alternatively, it is possible that the conjugated additive brings about a bulk change in the base oil that aids solubility of the drug.

The conjugated additive allows the free drug to be held within the tamponade reservoir, which means the drug may be delivered directly to the area that it is likely to have the greatest therapeutic benefit. The release of the drug may also be modified by the presence of the conjugated additive.

The conjugated additive is advantageous because in the event that the chain might be cleaved, its degradation products, namely the base oil and the hydrophobic moiety, are non-toxic. Further, the base oil part of the additive may be chemically similar to the surrounding tamponade and/or the hydrophobic part of the additive may be similar to the drug that is present. In particular, a specific advantage of the present invention is that the degradation products are non-toxic, and they may also have a therapeutic utility.

Administration and Treatment

The present invention provides a method of preventing or treating an eye disorder in a human or animal subject. The present invention also provides compositions for use in a method of preventing or treating an eye disorder in a human or animal subject. The present invention also provides compositions for use in a method of manufacturing a medicament for preventing or treating an eye disorder in a human or animal subject. The methods, uses in methods and compositions disclosed herein may comprise administering to the human or animal subject a therapeutically effective amount of the composition, as defined in the present invention.

In one arrangement, the eye disorder may be a retinal disease, condition or disorder, such as proliferative retinal pigment epithelium diseases, a detached retina, a torn retina or a disease, condition or disorder associated with an abnormality in the retinal pigment epithelium or its function. In another arrangement, the eye disorder may be proliferative vitreoretinopathy, retinal pigment epithelium cell proliferation or proliferative diabetic retinopathy. In a further arrangement, the detached or torn retina may be caused by rhegmatogenous retinal detachment, exudative retinal detachment, or tractional retinal detachment.

The composition of the present invention involves administration of a drug of the present invention to a subject. The drug may be administered in a therapeutically effective amount.

The composition of the invention may act as a tamponade. It is however not essential for the composition to act as a tamponade, or to act as a tamponade on its own: optionally a relatively small amount of composition may be used for the purpose of delivering a drug.

The term "therapeutically effective amount" or "therapeutically effective dose" as used herein refers to an amount of a drug needed to: treat; ameliorate; prevent the targeted disease condition; exhibit a detectable therapeutic or preventative effect. Toxicity and therapeutic efficacy of drugs can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The therapeutically effective amount or therapeutically effective dose is the amount of the drug that will elicit the biological or medical response of a tissue, system, animal, or human that is being sought by the researcher, veterinarian, medical doctor, or other clinician. For example, anti-proliferative activity or anti-inflammatory activity in the treatment and/or prevention of eye disorders, e.g. proliferative vitreoretinopathy.

Dosages preferably fall within a range of circulating concentrations that includes the $ED_{50}$ with little or no toxicity. Dosages may vary within this range. The exact formulation and dosage should be chosen according to methods known in the art, in view of the specifics of a patient's condition.

Dosage amount may be adjusted individually to provide levels of the active moiety that are sufficient to achieve the desired effects, i.e., minimal effective concentration (MEC). The MEC will vary for each compound but can be estimated from, for example, in vitro data and animal experiments. Dosages necessary to achieve the MEC will depend on individual characteristics and route of administration.

In general, the therapeutically effective dose/amount can be estimated by using conventional methods and techniques that are known in the art. Initial doses used in animal studies (e.g. non-human primates, mice, rabbits, dogs, or pigs) may be based on effective concentrations established in cell culture assays. The animal model may also be used to determine the appropriate concentration range. Such information can then be used to determine useful doses in human patients.

The specific dosage level required for any particular patient will depend on a number of factors, including severity of the condition being treated, the general health of the patient (i.e. age, weight and diet), the gender of the patient, the time of administration, judgement of the prescribing physician and tolerance/response to therapy. In general, however, the drug may be present in an amount of from about 1 to about 1000 µg per ml, from about 5 to about 900 µg per ml, from about 10 to about 800 µg per ml, from about 15 to about 700 µg per ml, from about 20 to about 600

μg per ml, from about 25 to about 500 μg per ml, or from about 30 to about 400 μg per ml.

In one arrangement, the drug may be released over a period of from about 2 to about 10 weeks, from about 3 to about 9 weeks, from about 4 to about 8 weeks, or from about 5 to about 7 weeks. In another arrangement, the drug may be released over a period of about 2, about 3, about 4, about 5, about 6, about 7, about 8, about 9 or about 10 weeks.

The present compositions may, if desired, be provided in a pack or dispenser device containing one or more unit dosage forms containing the composition. Such a pack or device may, for example, comprise metal or plastic or glass and rubber stoppers, such as in vials. Alternatively, the device may be a pre-loaded syringe and the pack may comprise one or more pre-loaded syringes. The pack or dispenser device may be accompanied by instructions for administration. The compositions of the invention may be formulated in a compatible pharmaceutical carrier or they may also be prepared, placed in an appropriate container, and labelled for treatment of an indicated condition.

It will be understood that any combination of doses and time periods is envisaged by the disclosure herein. For example, the drug may be present in in an amount of from about 1 to about 1000 μg per ml and released over a period of from about 2 to about 10 weeks. Similarly, the drug may be present in in an amount of from about 10 to about 800 μg per ml and released over a period of from about 4 to about 8 weeks.

Definitions

In the interests of simplicity, terms which are normally used to refer to monovalent groups (such as "alkyl" or "alkenyl") are also used herein to refer to divalent, trivalent or tetravalent bridging groups which are formed from the corresponding monovalent group by the loss of one or more hydrogen atom(s). Whether such a term refers to a monovalent group or to a polyvalent group will be clear from the context. Where a polyvalent bridging group is formed from a cyclic moiety, the linking bonds may be on any suitable ring atom, subject to the normal rules of valency.

Reference herein to "ibuprofen" is a reference to (RS)-2-(4-(2-Methylpropyl)phenyl)propanoic acid, which is shown below.

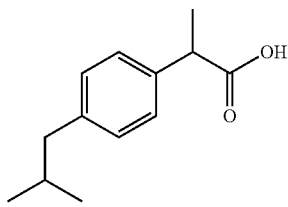

Reference herein to "all-trans retinoic acid" is a reference to (2E,4E,6E,8E)-3,7-Dimethyl-9-(2,6,6-trimethylcyclohexen-1-yl)nona-2,4,6,8-tetraenoic acid, which is shown below.

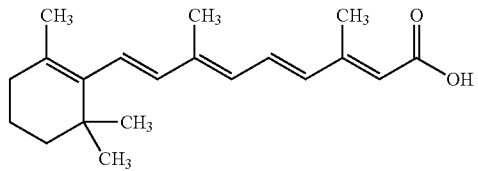 [SMILES: CC1=C(/C=C/C(C)=C/C=C/C(C)=C/C(=O)O)C(C)(C)CCC1]

The use of the word "a" or "an" when used in conjunction with the term "comprising" in the claims and/or the specification may mean "one," but it is also consistent with the meaning of "one or more," "at least one," and "one or more than one". Throughout this application, the term "about" is used to indicate that a value includes the inherent variation of error for the device, the method being employed to determine the value.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open ended and do not exclude additional, un-recited elements or method steps.

The terms "comprising" encompasses the term "consisting" e.g. a composition "comprising" X may consist exclusively of X or may include something additional e.g. X+Y, and "consisting essentially of", e.g. a composition "comprising" X may consist essentially of X or may include X and an additional amount of one or more impurities for example.

"Optional" or "optionally" means that the subsequently described event or circumstances may or may not occur, and that the description includes instances where said event or circumstance occurs and instances in which it does not.

"May" means that the subsequently described event of circumstances may or may not occur, and that the description includes instances where said event or circumstance occurs and instances in which it does not.

Where the compounds according to this invention have at least one chiral centre, they may accordingly exist as enantiomers. Where the compounds possess two or more chiral centres, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

It is to be understood that all such isomers and mixtures thereof are encompassed within the scope of the present invention.

As used herein, the term "substituted" is contemplated to include all permissible substituents of organic compounds. In a broad aspect, the permissible substituents include acyclic and cyclic, branched and unbranched, carbocyclic, aromatic and nonaromatic substituents of organic compounds. The permissible substituents may be one or more and the same or different for appropriate organic compounds. In one aspect of the invention, the substituents may include, an amine group (—NR$_2$, where R may be independently selected from H or OH), an amide group (—C(═O)NRR', where R and R' are independently selected from H, a C$_{1-10}$ alkyl group, a C$_{2-10}$ alkenyl group, a C$_{7-25}$ alkyl-aryl group, or a C$_{8-25}$ alkenyl-aryl group), a carboxylic acid group (—COOH), an ester group (—COOR, where R is selected from a C$_{1-10}$ alkyl group, a C$_{2-10}$ alkenyl group, a C$_{7-25}$ alkyl-aryl group, or a C$_{8-25}$ alkenyl-aryl group), a C$_{1-10}$ alkyl group, and a $C_{2-10}$ alkenyl group. In another arrangement, the substituents may include a carboxylic acid group (—COOH), a $C_{1-10}$ alkyl group, and a $C_{2-10}$ alkenyl group. Where more than one substitution occurs, it may be at the same position, adjacent to another or remote from the same position, i.e. separated by 0, 1, 2, 3, 4, 5, 6, 7, 8, 9, 10 or more carbon atoms.

Where any particular moiety is substituted, for example a phenyl group comprising a substituent on the aryl ring, unless specified otherwise, the term "substituted" contemplates all possible isomeric forms. For example, a substituted phenyl group includes all of the following ortho-, meta- and para-permutations:

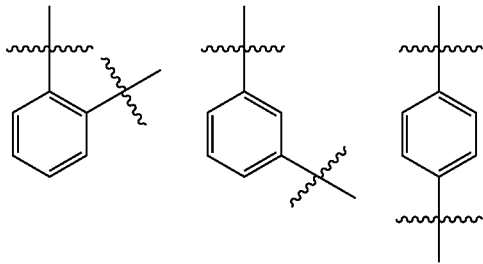 [SMILES: *c1ccccc1* ; *c1cccc(*)c1 ; *c1ccc(*)cc1]

Furthermore, the term "substituted" comprehends a substitution that may be adjacent or remote to the point of attachment of the group being substituted to the rest of the molecule.

It also comprehends the group being the point of attachment to the rest of the molecule.

Where a group comprises two or more moieties defined by a single carbon atom number, for example, $C_{7-25}$ alkyl-aryl, the carbon atom number indicates the total number of carbon atoms in the group.

As used herein, the term "alkyl" refers to a cyclic, straight or branched saturated monovalent hydrocarbon radical, having the number of carbon atoms as indicated. For example, the term "$C_{1-25}$ alkyl" includes $C_1$, $C_2$, $C_3$, $C_4$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$ and $C_{25}$ alkyl groups. Similarly, "$C_{1-10}$ alkyl" includes $C_1$, $C_2$, $C_3$, $C_4$, $C_4$, $C_5$, $C_6$, $C_7$, $C_8$, $C_9$, $C_{10}$ alkyl groups. By way of non-limiting example, suitable straight-chain and branched-chain alkyl groups include methyl, ethyl, propyl, iso-propyl, butyl, iso-butyl, tert-butyl, pentyl, hexyl, octyl and nonyl, suitable cyclic-alkyl groups include cyclopropyl, cyclobutyl, cyclopentyl, cyclohexyl, methylcyclohexyl, dimethylcyclohexyl, trimethylcyclohexyl, cycloheptyl, cyclooctyl, cyclononyl, and adamantyl, cyclopropylmethyl, cyclopropylethyl, cyclobutylmethyl, cyclobutylethyl, cyclopentylmethyl, cyclopentylethyl, cyclopentylpropyl, cyclohexylmethyl, cyclohexylethyl, cyclohexylpropyl, cyclohexylbutyl, methylcyclohexylmethyl, dimethylcyclohexylmethyl, trimethylcyclohexylmethyl, cycloheptylmethyl, cycloheptylethyl and cycloheptylpropyl. In one aspect of the present invention ranges of alkyl groups may be: $C_{1-25}$ alkyl, $C_{2-24}$ alkyl, $C_{3-23}$ alkyl, $C_{4-22}$ alkyl, $C_{5-21}$ alkyl, $C_{6-20}$ alkyl, $C_{7-20}$ alkyl, $C_{8-20}$ alkyl, $C_{9-20}$ alkyl, $C_{10-20}$ alkyl, $C_{11-20}$ alkyl, $C_{12-20}$ alkyl, $C_{13-20}$ alkyl, $C_{14-20}$ alkyl, $C_{15-20}$ alkyl, $C_{16-20}$ alkyl, $C_{17-20}$ alkyl and $C_{18-20}$ alkyl. In another aspect of the present invention ranges of alkyl groups may be: $C_{1-10}$ alkyl, $C_{2-9}$ alkyl, $C_{3-8}$ alkyl, $C_{4-7}$ alkyl, $C_{4-6}$ alkyl and $C_{5-7}$ alkyl.

As used herein, the term "alkenyl" refers to a cyclic, straight or branched unsaturated monovalent hydrocarbon radical, having the number of carbon atoms as indicated, and the distinguishing feature of a carbon-carbon double bond that is in the cis- or trans-configuration. In one aspect of the invention, the carbon chain may comprise more than one double bond, e.g. one, two, three, four, five, six, seven, eight or nine double bonds, wherein the one or more double bonds may be in the cis-, trans-configuration or a mixture thereof. For example, the term "$C_{2-25}$ alkenyl" includes $C_2$, $C_3$, $C_4$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$ and $C_{25}$ alkenyl groups. Similarly, $C_{2-10}$ alkenyl includes $C_2$, $C_3$, $C_4$, $C_4$, $C_5$, $C_6$, $C_7$, $C_8$, $C_9$, $C_{10}$ alkenyl groups. By way of non-limiting example, suitable alkenyl groups include ethenyl, propenyl, butenyl, penentyl, hexenyl, octenyl, nonenyl, cyclopentenyl, cyclohexenyl, nonadienyl, nonatrienyl and nonatetraenyl, wherein the double bond(s) may be located anywhere in the carbon chain. In one aspect of the present invention ranges of alkenyl groups may be: $C_{2-24}$ alkenyl, $C_{3-23}$ alkenyl, $C_{4-22}$ alkenyl, $C_{5-21}$ alkenyl, $C_{6-20}$ alkenyl, $C_{7-20}$ alkenyl, $C_{8-20}$ alkenyl, $C_{9-20}$ alkenyl, $C_{10-20}$ alkenyl, $C_{11-20}$ alkenyl, $C_{12-20}$ alkenyl, $C_{13-20}$ alkenyl, $C_{14-20}$ alkenyl, $C_{15-20}$ alkenyl, $C_{16-20}$ alkenyl, $C_{17-20}$ alkenyl and $C_{18-20}$ alkenyl. In another aspect of the present invention ranges of alkenyl groups may be: $C_{2-10}$ alkenyl, $C_{3-9}$ alkenyl, $C_{4-8}$ alkenyl, $C_{5-7}$ alkenyl and $C_{5-6}$ alkenyl.

As used herein, the term "aryl" refers to monovalent unsaturated aromatic carbocyclic radical having one, two, or three rings, which may be fused or bicyclic. In one aspect of the present invention, the term "aryl" refers to an aromatic monocyclic ring containing 5 or 6 carbon atoms, which may be substituted on the ring with 1, 2, 3, 4 or 5 substituents as defined herein; an aromatic bicyclic or fused ring system containing 7, 8, 9 or 10 carbon atoms, which may be substituted on the ring with 1, 2, 3, 4, 5, 6, 7, 8 or 9 substituents as defined herein; or an aromatic tricyclic ring system containing 10 carbon atoms, which may be substituted on the ring with 1, 2, 3, 4, 5, 6, 7, 8, 9, 10, 11, 12 or 13 substituents as defined herein. By way of non-limiting example, suitable aryl groups include phenyl, biphenyl, indanyl, azulenyl, tetrahydronaphthyl, tolyl, tolylphenyl and benzocycloheptyl. In one aspect of the present invention ranges of aryl groups are: $C_{5-10}$-aryl, $C_{5-9}$-aryl, $C_{6-8}$-aryl and $C_{6-7}$-aryl.

As used herein, the term "alkyl-aryl" refers to an alkyl group with an aryl substituent. Binding is through the alkyl group. Such groups have the number of carbon atoms as indicated. The aryl and alkyl moieties of such a group may be substituted as defined herein, with regard to the definitions of aryl and alkyl. The alkyl moiety may be straight or branched. Typical examples of aryl-alkyl include benzyl, methylbenzyl, ethylbenzyl, dimethylbenzyl, diethylbenzyl, methylethylbenzyl, phenethyl, phenylpropyl, phenylbutyl, propylbenzyl, tolylmethyl, phenylethylbenzyl, isopropylbenzyl, diphenylmethyl, propylbenzyl, butylbenzyl, dimethylethylbenzyl, phenylethyl, phenylpropyl, phenyl-isopropyl, phenyl-n-butyl, phenyl-iso-butyl, phenyl-tert-butyl, phenylpentyl, tetramethylbenzyl, phenylhexyl, dipropylbenzyl, triethylbenzyl, cyclohexylbenzyl, naphthylmethyl, diphenylethyl, triphenylmethyl and hexamethylbenzyl.

With regard to one or more substituents which are referred to as being on the carbon backbone of a group with a compound definition, for example, "alkyl-aryl", the substituent may be on either or both of the component moieties, e.g., on the alkyl and/or aryl moieties.

Reference to cyclic systems, e.g., aryl, cycloalkyl, etc., contemplates monocyclic and polycyclic systems. Such systems comprise fused, non-fused and spiro conformations, such as bicyclooctyl and adamantyl.

Other "compound" group definitions will be readily understandable by the skilled person based on the previous definitions and the usual conventions of nomenclature.

The term "SiO" refers to silicone oil. For example, $SiO_{1000}$ refers to a silicone oil having a kinematic viscosity of 1000 CSt, and $SiO_{5000}$ refers to a silicone oil having a kinematic viscosity of 5000 CSt. Similarly, $SiO_{1000-5000}$ refers to a Silicone oil having a kinematic viscosity of from 1000-5000 CSt.

All rheological measurements, including measurement of kinematic viscosity, were carried out using a TA Instruments Rheolyst AR 1000 N controlled-stress rheometer (TA Instruments, Elstree, United Kingdom). A 50 mm diameter, 4° steel cone geometry was used. All measurements were carried out at 37° C. Temperature control of the rheometer is achieved via a plate that utilises the Peltier effect to control the temperature of the sample within ±0.1° C. Shear viscosity was calculated from the gradient of the plot of shear stress against shear rate.

The present invention will now be described by way of example with reference to the following examples and figures:

FIG. 1 is a NMR spectrum of conjugated all-trans retinoic acid according to the present invention;

FIG. 2 shows a comparison of saturation concentration of atRA measured in SiO via UV-vis or radioactivity measurements. Literature values are taken from J. J. Araiz, M. F. Refojo, M. H. Arroyo, F. L. Leong, D. M. Albert and F. I. Tolentino, *Investigative Ophthalmology & Visual Science*, 1993, 34, 522-530. The error bars show ±1 standard deviation;

EXAMPLES

List of Abbreviations

Figure 1:
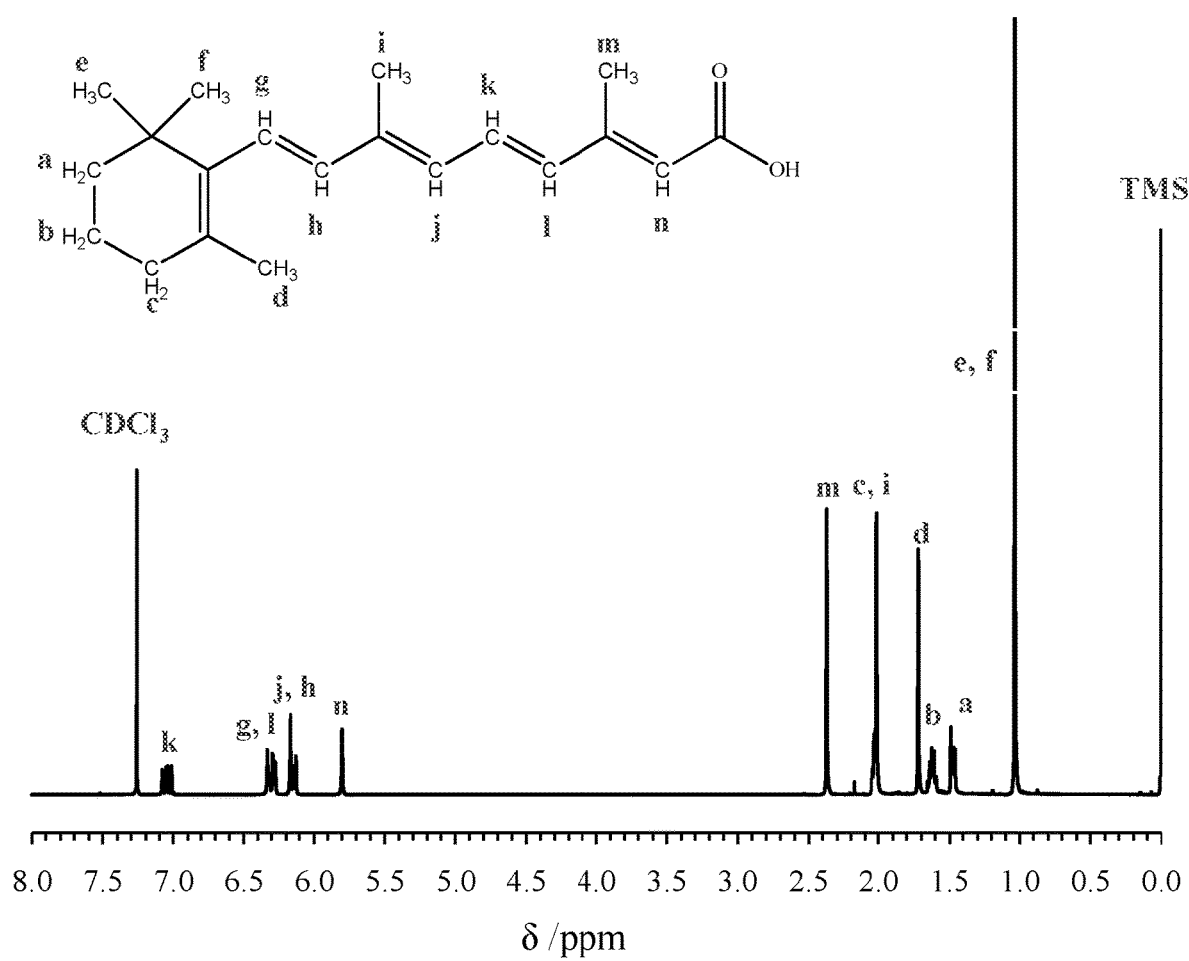

5-FU 5-Fluorouracil
ACN Acetonitrile
Ar Argon
atRA All-trans Retinoic Acid
BA Benzoic Acid
bFGF Basic Fibroblast Growth Factor
BrdU Bromodeoxyrubicin
$CDCl_3$ Deuterated Chloroform
CDI 1,1'-Carbonyldiimidazole
$D_2O$ Deuterium Oxide
DAPI Dianidine-2-Phenylindole
DCC Dicyclohexylcarbodiimide
DCI Deuterium Chloride
DCM Dicholoromethane
DCU Dicyclohexylurea
DMAP 4-(Dimethylamino)pyridine
DMF Dimethylformamide
DMSO Dimethyl Sulfoxide
EPGF Epidermal Growth Factor
FGF Fibroblast Growth Factor
FSiO Fluorinated Silicone Oil
HCl Hydrochloric Acid
Ibu Ibuprofen
IF-γ Interferon-Gamma
IL- Interlukin
IPA Isopropanol
MeOH Methanol
MTT 3-(4,5-Dimethylthiazol-2-yl)-2,5-Diphenyltetrazolium Bromide
PDMS Poly(dimethylsiloxane)
PDMS-diOH Bis(hydroxyalkyl) Terminated Poly(dimethylsiloxane)
PDGF Platelet-Derived Growth Factor
RA Retinoic Acid
SFA Semi-Fluorinated Alkane
SiO Silicone Oil
TAA Triamcinolone Acetonide
TGF-β Tumour Growth Factor-Beta
THF Tetrahydrofuran
VEGF Vascular Endothelial Growth Factor Preparation Steglich Esterification Reaction The hydrophobic moiety may be prepared by an esterification reaction between the hydrophobic moiety and the poly(dimethylsiloxane) part of the additive. The esterification reaction may be Steglich esterification reaction, which is a variation of a classic esterification, using dicyclohexylcarbodiimide as a coupling reagent and 4-dimethylaminopyridine as a catalyst.

Dicyclohexylcarbodiimide and the carboxylic acid form an O-acylisourea intermediate, which offers reactivity similar to the corresponding deprotonated carboxylic acid. The alcohol can then be added to the activated carboxylic acid to liberate the stable dicyclohexylurea and the ester; however this reaction is very slow in comparison to esterifications where strong nucleophiles such as amines are used. The reaction with alcohol is slow enough that it allows the isolation of the O-acylisourea which then remains as a side product. The reaction's success comes from the addition of 4-dimethylaminopyridine, a stronger nucleophile than an alcohol, which acts as an acyl transfer agent to form an activated amide ("active ester"). The alcohol then reacts quickly with this intermediate to form the desired ester.

atRA-PDMS-atRA

Bis(hydroxyalkyl) terminated poly(dimethylsiloxane), ($M_n$=4,700 gmol$^{-1}$, 4 g, 1.7 mmol OH) was dissolved in degased DCM (10 mL), followed by the addition of a degased solution of atRA (0.6 g, 2 mmol) and DMAP (64 mg, 0.5 mmol) in DCM (30 mL). Finally 10 mL of a degased solution of DCC (0.41 g, 2 mmol) in DCM was added. This mixture was stirred at room temperature, under argon (Ar), in the dark, for 4 days. After filtration of the residual DCU, the solvent was eliminated under reduced pressure. The residual yellow oil was washed three times with cold methanol then dried in vacuo. The purified yellow oil was filtered through a 0.45 pm PTFE filter, then stored under Ar in dark conditions at ambient temperature. atRA-PDMS-atRA was analyzed by $^1$H NMR and FTIR. $^1$H NMR (400 MHz, CDCl$_3$): δ 7.00 (q, 1H×2, =CH—C$\underline{H}$=CH), 6.29-6.11 (4H×2, =C$\underline{H}$—C—CH$_3$, —C$\underline{H}$=C—CH$_3$ and C—C$\underline{H}$=C$\underline{H}$—C—CH$_3$), 5.82/5.69 (s, 1H×2, —OC$\overline{O}$C$\underline{H}$=C), 4.26 (t, 2H×2, O—CH$_2$—C$\underline{H}_2$—OCO), 3.66 (t, $\overline{2}$H×2, O—CH$_2$—C$\underline{H}_2$—OCO), 3.44 (t, 2H×2, Si—CH$_2$—CH$_2$—C$\underline{H}_2$—O), 2.35 (s, 3H×2, C(C$\underline{H}_3$)=CH—C(O)O), 2.02 (t, 2H'2, C$\underline{H}_2$—C(CH$_3$)=C), 2.00 (s, 3H×2, C(C$\underline{H}_3$)=CH—CH=CH), 1.71 (s, 3H×2, CH$_2$—C(C$\underline{H}_3$)=C), 1.61 (m, 2H×2, 2H×2, Si—CH$_2$—C$\underline{H}_2$—CH$_2$—O, CH$_2$—C$\underline{H}_2$—CH$_2$—C(CH$_3$)=C), 1.47 (m, 2$\overline{H}$×2, C$\underline{H}_2$—CH$_2$—CH$_2$—C(CH$_3$)=C), 1.02 (s, 6H×2, CH$_2$—C(C$\underline{H}_3$)$_2$—C), 0.54 (qt, 2H×2, Si—C$\underline{H}_2$—CH$_2$—CH$_2$—O), 0.07 (s, 6H×n, Si(C$\underline{H}_3$)$_2$—O). IR: 1,738 cm$^{-1}$ $\cup_{(C=O)}$ in ester.

Ibu-PDMS-Ibu

Bis(hydroxyalkyl) terminated poly(dimethylsiloxane) (M$_n$=4,700 gmol$^{-1}$, 4 g, 1.7 mmol OH), ibuprofen (0.4 g, 1.9 mmol) and DMAP (30 mg, 0.24 mmol) were dissolved in DCM (15 mL), followed by addition of a 10 mL DCC (0.4 g, 1.9 mmol) solution in DCM. This mixture was stirred at room temperature for 24 hours. After filtration of the residual DCU, the solvent was eliminated under reduced pressure. The residual colourless oil was washed two times with room temperature methanol then dried in vacuo. The purified oil was filtered through a 0.45 μm PTFE filter. Ibu-PDMS-Ibu was analyzed by $^1$H NMR and FTIR. $^1$H NMR (400 MHz, CDCl$_3$): δ 7.21/7.08 (d, 4H×2, C$\underline{H}$ from aromatic ring), 4.21 (m, 2H×2, O—CH$_2$—C$\underline{H}_2$—OCO), 3.73 (q, 1H×2, OC(O)—C$\underline{H}$(CH$_3$)—C), 3.57 (t, 2H—2, O—C$\underline{H}_2$—CH$_2$—OCO), 3.35 (t, 2H—2, Si—CH$_2$—CH$_2$—C$\underline{H}_2$—O), 2.43 (d, 2H×2, C—C$\underline{H}_2$—CH(CH$_3$)$_2$), 1.83 (m, 1$\overline{H}$×2, C—CH$_2$—C$\underline{H}$(CH$_3$)$_2$), 1.57 (m, 2H×2, Si—CH$_2$—C$\underline{H}_2$—CH$_2$—O), 1.49 (d, 3H×2, OC(O)—CH(C$\underline{H}_3$)—C), 0.89 (d, 6H×2, C—CH$_2$—CH(C$\underline{H}_3$)$_2$), 0.50 (t, 2H×2, Si—C$\underline{H}_2$—CH$_2$—CH$_2$—O), 0.07 (s, 6$\overline{H}$—n, Si(C$\underline{H}_3$)$_2$—O). IR: 1,738 cm$^{-1}$ $\cup_{(C=O)}$ in ester.

Anhydride Route

Preparation of atRA Anhydride atRA (2 g, 66 mmol) and DCC (1 g, 34 mmol) were dissolved in DCM (20 mL) and the reaction mixture was gently stirred at ambient temperature in the dark for 2 days. After filtration of the mixture and removal of the DCM in vacuo, the final product was isolated with a 67% yield and analysed by $^1$H and $^{13}$C NMR spectroscopy. $^1$H NMR (400 MHz, CDCl$_3$): δ 7.00 (q, 1H×2, =CH—C$\underline{H}$=CH), 6.29-6.11 (4H×2, =C$\underline{H}$—C—CH$_3$, —C$\underline{H}$=C—CH$_3$ and C—C$\underline{H}$=C$\underline{H}$—C—C$\overline{H}_3$), 5.82/5.69 (s, 1H×2, —OC$\overline{O}$C$\underline{H}$=C), 2.35 (s, 3H×2, C(C$\underline{H}_3$)=CH—C(O)O), 2.02 (t, 2$\overline{H}$×2, C$\underline{H}_2$—C(CH$_3$)=C), 2.00 (s, 3H×2, C(C$\underline{H}_3$)=CH—CH=CH), 1.71 (s, 3H×2, CH$_2$—C(C$\underline{H}_3$)=C), 1.61 (m, 2H×2, 2H×2, C$\underline{H}_2$—CH$_2$—CH$_2$—O, C$\underline{H}_2$—CH$_2$—CH$_2$—C(CH$_3$)=C), 1.47 (m, 2H×2, C$\underline{H}_2$—CH$_2$—CH$_2$—C(CH$_3$)=C), 1.02 (s, 6H×2, CH$_2$—C(C$\underline{H}_3$)$_2$—C). $^{13}$C NMR (100 MHz, CDCl$_3$): δ 163 ($\underline{C}$=O), 156 ($\underline{C}$H$_2$—C(CH$_3$)=C), 141 (—C—$\underline{C}$(CH)=C—), 138 (C=$\underline{C}$(H)—C—), 137 (CH—C(CH$_3$)=C—), 135 (CH=$\underline{C}$(H)—C—), 132 (C—$\underline{C}$(CH$_3$)=C—), 130 (C=$\underline{C}$H—$\overline{C}$—, C), 118 (C=$\underline{C}$H—C(O)), 40 (C—$\underline{C}$H$_2$—C), 35 (C—$\underline{C}$(CH$_3$)$_2$), 34 (C—$\underline{C}$H$_2$—C=C), 29 (2×CH$_3$ off ring), 22 (CH$_3$ off ring), 20 (CH$_2$—$\underline{C}$H$_2$—CH$_2$), 14 (C$\underline{H}_3$ chain), 13 (C$\underline{H}_3$ chain near C=O).

Preparation of atRA-PDMS-atRA

Poly(dimethylsiloxane) bis(hydroxyalkyl) terminated (M$_n$=4,700 gmol$^{-1}$, 3 g, 1.2 mmol OH) was dissolved in degased DCM (10 mL), followed by the addition of a degased solution of atRA anhydride synthesised in the previous step (1.06 g, 1.8 mmol) and DMAP (37 mg, 0.25 mmol) in DCM:Pyridine (30 mL 1:1 v/v). This mixture was stirred at room temperature, under Ar and in the dark for 4 days. After this time approximately 2 mL of water was added to quench the excess anhydride and the mixture was stirred for a further 2 hours. The product was purified by diluting the mixture with DCM (150 mL) and washing it with 1 M NaHSO$_4$ (3×150 mL), 1 M NaHCO$_3$ then brine (2×150 mL). The organic layer was dried over MgSO$_4$ and the solvent was removed in vacuo. The remaining oil was washed with MeO H (5×30 mL) to remove unattached atRA then dried in vacuo. The purified yellow oil was filtered through a 0.45 μm PTFE filter, then stored under Ar in dark conditions. atRA-PDMS-atRA was analyzed by $^1$H NMR. $^1$H NMR (400 MHz, CDCl$_3$): δ 7.00 (q, 1H ×2, =CH—C$\underline{H}$=CH), 6.29-6.11 (4H×2, =C$\underline{H}$—C—CH$_3$, —C$\underline{H}$=C—C$\overline{H}_3$ and C—C$\underline{H}$=C$\underline{H}$—C—C$\overline{H}_3$), 5.82/5.69 (s, 1H×2, —OC$\overline{O}$C$\underline{H}$=C), 4.26 (t, 2H×2, O—CH$_2$—C$\underline{H}_2$—OCO), 3.66 (t, $\overline{2}$H×2, O—CH$_2$—C$\underline{H}_2$—OCO), 3.44 (t, 2H×2, Si—CH$_2$—CH$_2$—C$\underline{H}_2$—O), 2.35 (s, 3H×2, C(C$\underline{H}_3$)=CH—C(O)O), 2.02 (t, $\overline{2}$H×2, C$\underline{H}_2$—C(CH$_3$)=C), 2.00 (s, 3H×2, C(C$\underline{H}_3$)=CH—CH=CH), 1.71 (s, 3H×2, CH$_2$—C(C$\underline{H}_3$)=C), 1.61 (m, 2H×2, 2H×2, Si—CH$_2$—C$\underline{H}_2$—CH$_2$—O, CH$_2$—C$\underline{H}_2$—CH$_2$—C(CH$_3$)=C), 1.47 (m, 2H×2, C$\underline{H}_2$—CH$_2$—CH$_2$—C(CH$_3$)=C), 1.02 (s, 6H×2, CH$_2$—C(C$\underline{H}_3$)$_2$—C), 0.54 (qt, 2H×2,Si—C$\underline{H}_2$—CH$_2$—CH$_2$—O), 0.07 (s, 6H×n, Si(C$\underline{H}_3$)$_2$—O).

Drug Solubility Measurement in SiO and Blends Utilising Radioisotopes

The process of using radiolabelled drugs to determine solubility concentration within SiO is a much simpler protocol than that used when UV-Vis was utilised as there is no longer the need for the extraction step.

atRA Solubility Studies

The saturation concentration of free atRA in SiO was investigated using the tritiated atRA. A saturated solution of atRA, spiked with tritiated atRA, in SiO was prepared and stirred gently. Samples were taken at different time-points then filtered using a syringe pump (4 mL/h) and 0.45 μm PTFE filters. To determine the amount of atRA dissolved in SiO, a 20 μL sample of oil was taken, which was insoluble in the scintillation cocktail, therefore, a co-solvent was needed to fully solvate the material for accurate analysis. After several tests using a known activity of sample, it was determined that a ratio of diethyl ether/scintillation cocktail (8:10 mL) allowed accurate activity measurement by liquid scintillation.

While the solubility reported for atRA in SiO$_{1000}$ in the literature is 20 μg/mL, higher concentrations, in the order of 28 μg/mL (9.5×10$^{-5}$ M, s.d.=1, n=6). were measured when the same protocol was used.L Using the tritiated atRA, the solubility measured was over 20 times higher than the previous values, reaching 450.6 μg/mL (1.5×10$^{-3}$ M, s.d.=39.9, n=4).

Figure 2:
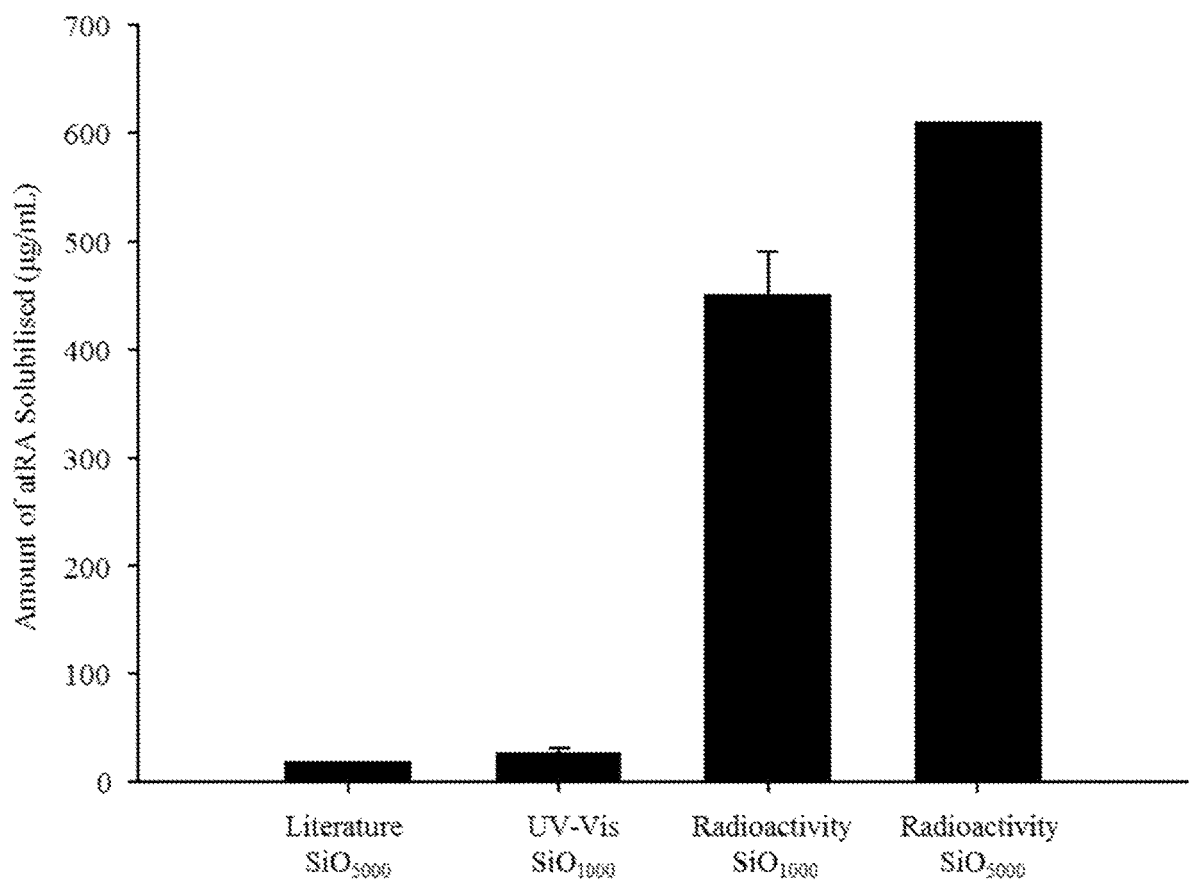

The solubility of atRA in SiO$_{5000}$ was also investigated as a simpler protocol was now in place to deal with such a viscous substance. Saturation was determined to be higher than in SiO$_{1000}$ at 610 µg/mL (2.03×10$^{-3}$ M, n=1) in SiO$_{5000}$. Results are shown in FIG. 2, which depicts a comparison of saturation concentration of atRA measured in SiO via UV-vis or radioactivity measurements. Error bars±1 standard deviation.

The use of radiolabelled isotopes has provided a much more accurate method to measure small drug concentration in SiO compared to the classic extraction combined with traditional instrumentation e.g. UV-Vis spectroscopy. However, such a large difference between methods was not anticipated. When the literature value was further analysed, it was noticed that the calibration curve used was in the range 0.5×10$^{-4}$ M to 1×10$^{-6}$ M, with the reported 20 µg/mL (0.6×10$^{-4}$ M) being on the cusp of the maximum value; therefore, higher concentrations need extrapolation from the curve, leading to potential errors. Overall an accurate method to measure solubility of atRA in SiO has been established using radiolabelling techniques and a fundamental inaccuracy in the published literature has been identified.

atRA in SiO Blends

The same protocol used to determine accurate atRA solubility in SiO was employed to determine free atRA concentration in blends of PDMS-atRA in SiO$_{1000}$ at 1, 5 and 10% (v/v). As the amount of PDMS-atRA present in the blend increased so did the measured saturation concentration of atRA (see Table 1). An increase from 450.6 µg/mL to 812.7 µg/mL was observed when a blend of 10% PDMS-atRA in SiO$_{1000}$ was used. This indicated the blends have a positive effect on the solubility of the free drug, increasing its saturation concentration in the oil possibly due to the presence of attached drug and its affinity towards free drug.

TABLE 1

Saturation amounts of atRA (µg/mL) in SiO$_{1000}$ and SiO$_{1000}$ blended with PDMS-atRA at 1, 5 and 10% (v/v) after 2 weeks at ambient temperature, in air.

|  | SiO | 1% PDMS-atRA | 5% PDMS-atRA | 10% PDMS-atRA |
|---|---|---|---|---|
| atRA (µg/mL oil) | 450.6 | 651.0 | 699.8 | 812.7 |
| atRA (M) | 1.50 × 10$^{-3}$ | 2.17 × 10$^{-3}$ | 2.33 × 10$^{-3}$ | 2.71 × 10$^{-3}$ |

The shear viscosity of SiO$_{1000}$ and SiO$_{5000}$, as well as the blends with end-modified PDMS, were measured at 37° C. (the temperature of cell culture within the project) and calculated from the gradient of the plot of shear stress against shear rate; graphs are shown in FIG. 3.

Figure 3:
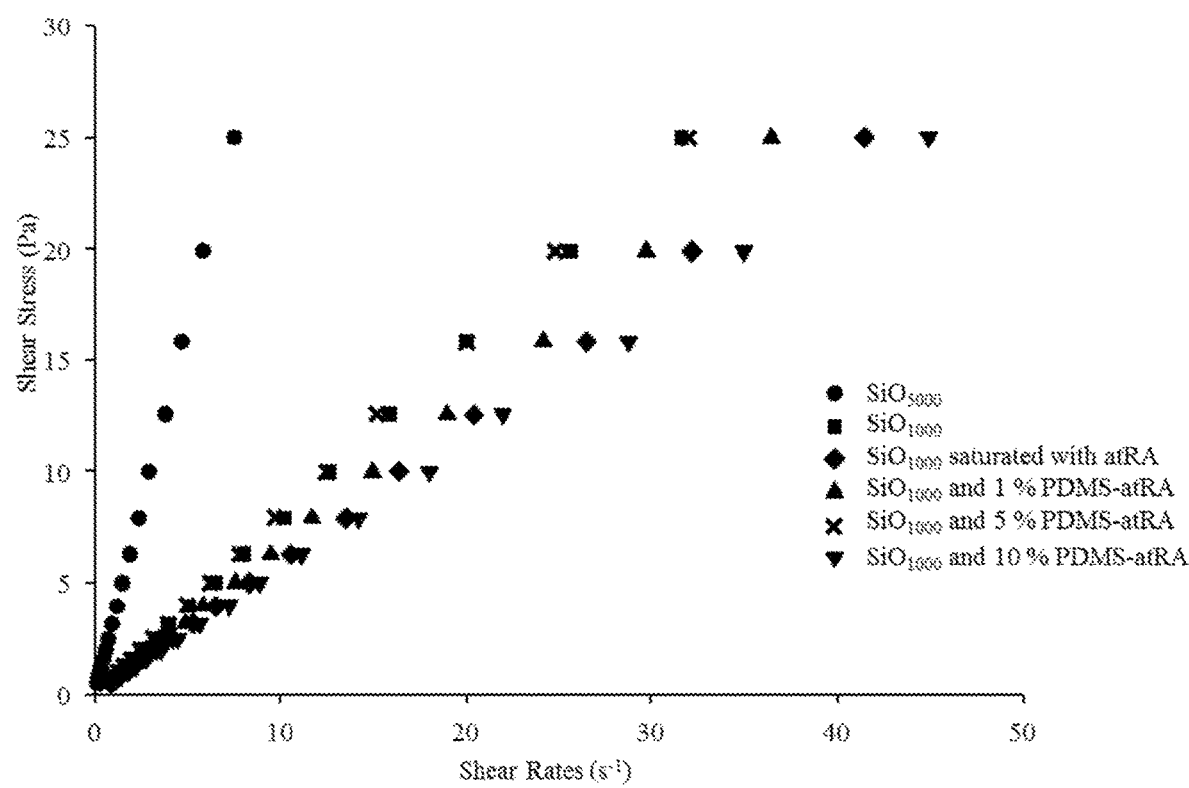
FIG. 3 is a graph of shear stress against shear rate for $SiO_{5000}$, $SiO_{1000}$, $SiO_{1000}$ saturated with atRA.

FIG. 3 depicts shear stress against shear rate for SiO$_{5000}$ (●), SiO$_{1000}$ (■), SiO$_{1000}$ saturated with atRA (◆), SiO$_{1000}$ blends with 1 (▲), 5 (x) and 10 (▼) % (v/v) PDMS-atRA from which the shear viscosity was calculated.

The measured viscosities show that there is a negligible effect of saturating SiO$_{1000}$ with atRA, and the viscosity of the blends do not follow a trend of decreasing or increasing viscosity, therefore, it is not characteristic variation in viscosity that is affecting the observed saturation concentration change within the blends, Table 2.

TABLE 2

Shear viscosities (mPa/s) calculated from the gradient of the plot of shear stress against shear rate at 37° C.

| Material | Shear Viscosity (mPa/s) at 37° C. |
|---|---|
| SiO$_{5000}$ | 3.35 |
| SiO$_{1000}$ | 0.79 |
| SiO$_{1000}$ saturated with atRA | 0.79 |
| SiO$_{1000}$ with 1% PDMS-atRA | 0.61 |
| SiO$_{1000}$ with 5% PDMS-atRA | 0.68 |
| SiO$_{1000}$ with 10% PDMS-atRA | 0.56 |

Release Studies

The effect of the presence of PDMS-drug on the release pattern of free drug was investigated within the atRA systems, with the potential that the affinity of the blend to the drug would result in a slower release compared to the short time periods stated in the literature; that is 98% clearance of atRA administered to the eye via a SiO tamponade, within a 7 day time period. This time period also needed to be confirmed, as the literature had already proven to be inaccurate in measuring atRA solubility in SiO and subsequent measurements could also be affected by inaccuracies. The optimum time period for release, targeted by this research, is 6 weeks as this is the clinical treatment period for PVR. Appropriate conditions of temperature, CO$_2$ content, and presence/absence of cells for these experiments were investigated.

Experimental Design for Drug Release Studies

The release of atRA from SiO$_{1000}$ and SiO$_{1000}$ blends with PDMS-drug (using solutions containing various initial concentrations) into culture media was monitored using tritiated versions of drugs. The experiments were designed as follows: 1 mL of oil or blend containing free drug was placed over 0.5 mL of culture media in a 24 well plate. The culture media was exchanged with fresh culture media when samples were taken, and the amount of drug in the media determined directly via liquid scintillation counting. 1:1 DMEM:F12 media containing 1% Pen-Strep, 1% Amphotericin B and supplemented with 10% FCS was used.

Quenching Effect of Culture Media in Liquid Scintillation

It is known that highly coloured samples can interfere with the scintillation counting process via quenching. The colour of the sample interferes with the light signals produced by the scintillant, therefore, leading to discrepancies in the data collected. To rule out potential inaccuracies, the effect of 250 µL of culture media within the scintillant cocktail (10 mL) was tested and showed no significant effect on the counts due to the solution being very dilute (see Table 3). For each 0.5 mL culture media sample collected throughout the experiments, 250 µL was analysed, and the total amount of drug released deduced from that.

TABLE 3

Decays per minute (DPM) of tritiated atRA solutions of both high and low concentration with and without media present.

|  | High Tritium Content (DPM) | | | Low Tritium Content (DPM) | | |
|---|---|---|---|---|---|---|
| Without Media | 11,702 | 12,361 | 12,282 | 308 | 458 | 348 |
| With Media | 11,566 | 12,521 | 12,237 | 281 | 429 | 306 |
| Difference | −136 | 160 | −45 | −27 | −29 | −42 |

Effect of Temperature on SiO

The shear viscosities of $SiO_{1000}$ were measured at 20, 30 and 37° C. (the approximate temperature of the eye) to determine if temperature would alter the rheological properties of the oil. The shear viscosities were calculated from the gradient of the plot of shear stress against shear rate. As a difference was observed (see Table 4), all release experiments were carried out at 37° C. as this is the temperature used to culture cells as well as a similar temperature observed in the eye.

TABLE 4

Shear viscosities (mPa/s) of $SiO_{1000}$ calculated from the gradient of the plot of shear stress against shear rate at 20, 30 and 37° C.

| Temperature (° C.) | Shear Viscosity (mPa/s) at 25 Pa |
|---|---|
| 20 | 1.0879 |
| 30 | 0.9115 |
| 37 | 0.7912 |

Effect of $CO_2$ on Release

The effect of atmospheric $CO_2$ content within the experiments on the release rate of atRA from SiO and blends into culture media was evaluated. A release experiment was carried out at 10% $CO_2$ (5% $CO_2$ is used to culture the cells) due to lack of availability of incubators that could hold radioisotopes. The same experiment was carried out in air, and the different release rates observed were compared.

Figure 4:
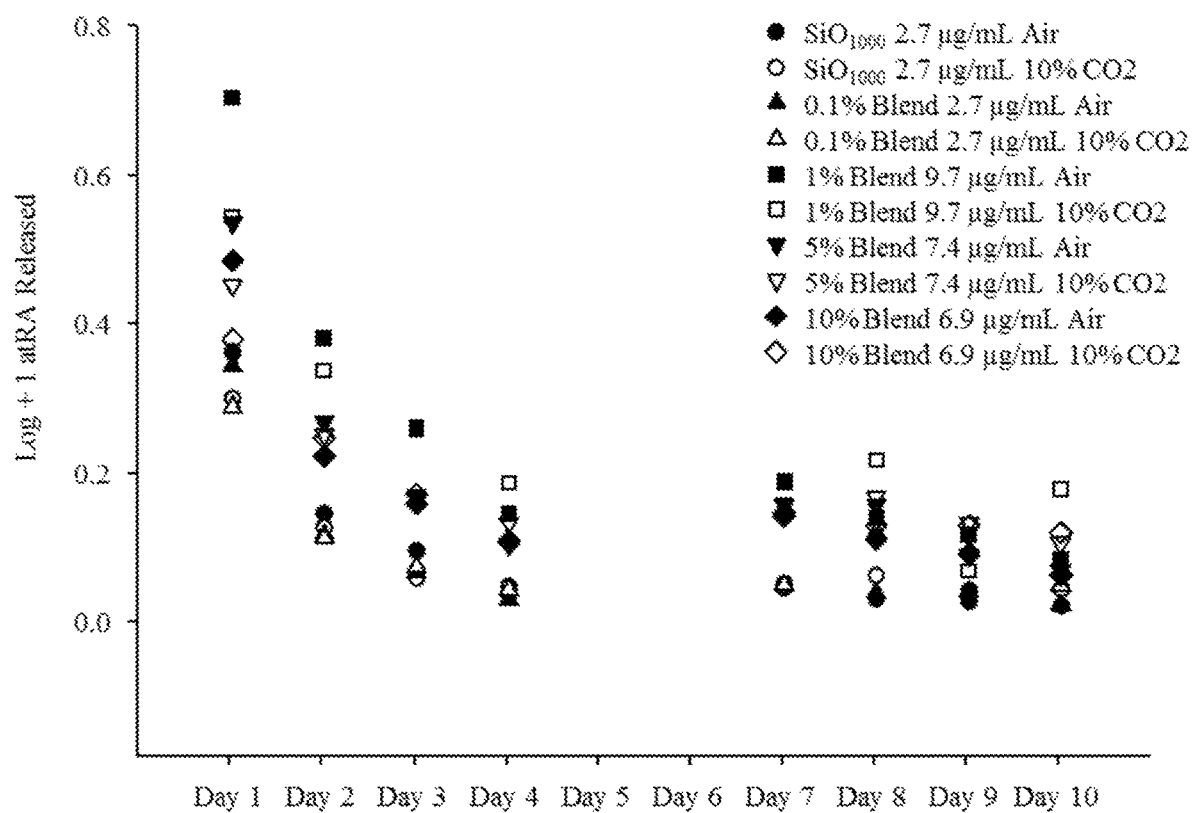
FIG. 4 shows release of atRA at a concentration below 10 μg/mL from $SiO_{1000}$ and blends of PDMS-atRA in $SiO_{1000}$ of different compositions (0.1, 1, 5 and 10% v/v) both in air (filled) and in a 10% $CO_2$ atmosphere (unfilled) into media.

FIG. 4 highlights differences in release from experiments conducted in air and within the presence of 10% $CO_2$. On day 1, more atRA was observed to be released when the experiment was carried out in air, however, this difference decreased by day 2, and by day 8 the opposite effect was observed with more atRA released under a 10% $CO_2$ atmosphere. Overall, this experiment showed that the atmospheric conditions for accurate release studies need to be kept constant to allow comparison.

As a consequence of the investigations of optimum experimental conditions, all following experiments were carried out at 37° C. in a 5% $CO_2$ atmosphere (the same conditions used for ARPE-19 cell culture).

Release of atRA at a concentration below 10 μg/mL from $SiO_{1000}$ (● and ○) and 0.1 (▲ and Δ), 1 (■ and □), 5 (▼ and ∇) and 10% (♦ and ◊) blends (v/v) both in air (filled) and in a 10% $CO_2$ atmosphere (unfilled) into media is shown in FIG. 4. All experiments were carried out at 37° C.

Effect of the Presence of Cells

Figure 5:
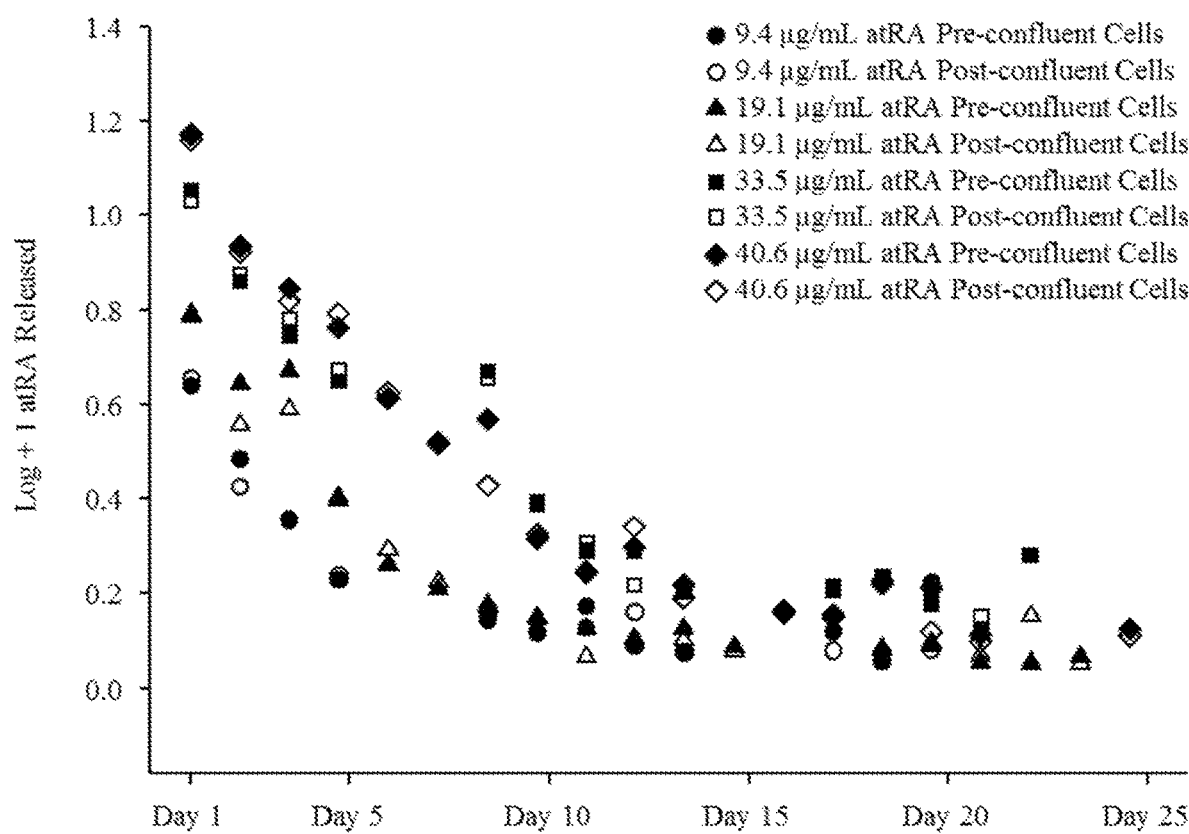
FIG. 5 shows release of atRA at various concentrations from $SiO_{1000}$ into media in the presence of pre- and post-confluent cells (filled and unfilled respectively) presented in a log+1 scale.

A release experiment of atRA in $SiO_{1000}$ into media in the presence of pre- and post-confluent cells (cultured for 1 day and 7 days respectively) was performed. This aimed to determine if the presence of cells had an impact on the drug release rate, as cells could act as a drain for released atRA and potentially affect the balance of concentrations. As seen in FIG. 5 no obvious differences in release rates were observed, therefore, future experiments could be carried out in the absence of cells.

Release of atRA at various concentrations from $SiO_{1000}$ into media in the presence of pre- and post-confluent cells (filled and unfilled respectively) presented in a log+1 scale is shown in FIG. 5. All experiments were carried out at 37° C. in a 5% $CO_2$ atmosphere.

Release Studies of atRA

Figure 6:
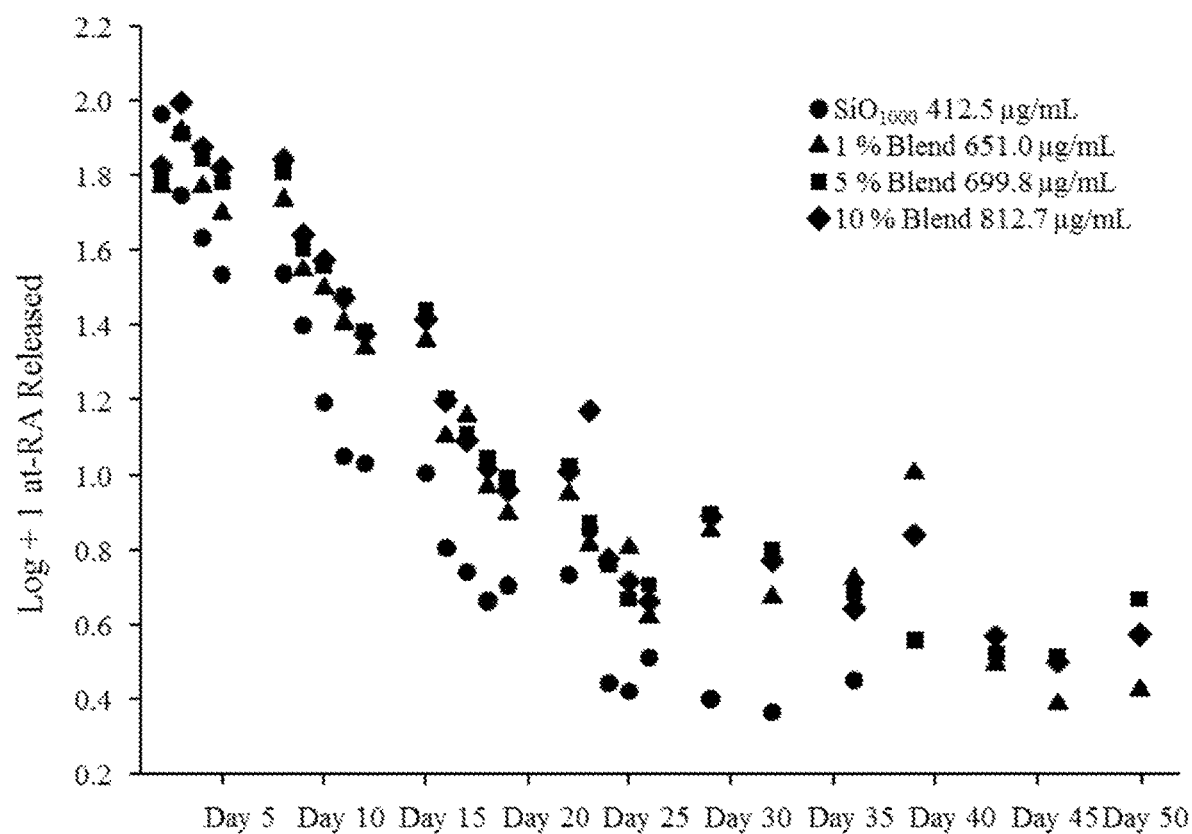
FIG. 6 shows release amounts of atRA from saturated $SiO_{1000}$ and saturated blends of PDMS-atRA in $SiO_{1000}$ of different compositions (1, 5 and 10% v/v) into culture media, presented on a log+1 scale.

The release into culture media of atRA from saturated $SiO_{1000}$ and blends (PDMS-atRA contents of 1, 5 and 10% in $SiO_{1000}$ (v/v)) was studied. As stated earlier, the saturation concentration of atRA increases with increasing amounts of PDMS-atRA, therefore, all starting concentrations within the experiments were slightly different as saturation conditions were employed. FIG. 6 displays the amount of atRA released over a 50 day period, presented with a log plot+1 scale; this scale was chosen so release points were easily comparable. A rapid release of atRA is observed within the first few days, after which the release gradually slows and then becomes steady over the remaining 20 days. More atRA appears to be released from the blends, probably due to initial saturation concentrations being higher.

Release amounts of atRA from saturated $SiO_{1000}$ (●), 1 (▲), 5 (■) and 10 (♦) % (v/v) blends of PDMS-atRA in $SiO_{1000}$ into culture media presented on a log+1 scale are shown in FIG. 6.

When looking at the amount of atRA released from $SiO_{1000}$ and the blends as a cumulative percentage (Table 5), it is very interesting to notice the difference in time taken for 80% of the solubilised atRA to be released: 2 weeks for $SiO_{1000}$ compared to nearly 7 weeks for the 10% blend. This is also interesting as the literature value of 7 days to clear 98% atRA from a saturated $SiO_{5000}$ solution has been disputed (although the 7 d time point was taken from a rabbit model rather than an in vitro model).

Although promising release time periods were observed, the amounts of atRA being initially released were above the toxic range for ARPE-19 cells ($10^{-4}$-$10^{-5}$ M). It was important to ascertain if the use of blends of SiO with PDMS-atRA could impact the release rate for lower concentrations of atRA to avoid the potential of toxicity, and if the longevity of the release period was dependant on the amount of atRA initially solubilised.

TABLE 5

Number of days needed to reach a certain percentage (cumulative) of release of atRA from saturated solutions of $SiO_{1000}$ and 1, 5 and 10% PDMS-atRA blends

| | Days Taken to Reach Percentage of Release | | | |
|---|---|---|---|---|
| Cumulative Percentage | $SiO_{1000}$ (412.5 μg/mL) | 1% Blend (651.0 μg/mL) | 5% Blend (699.8 μg/mL) | 10% Blend (812.7 μg/mL) |
| 10 | <1 | 1.1 | 1.1 | 1.2 |
| 20 | <1 | 1.9 | 1.8 | 1.8 |
| 30 | 1.6 | 2.9 | 2.9 | 3.1 |
| 40 | 2.4 | 4.2 | 4.1 | 4.2 |
| 50 | 3.3 | 7.2 | 6.8 | 7.2 |
| 60 | 5.4 | 9.8 | 9.2 | 9.9 |

TABLE 5-continued

Number of days needed to reach a certain percentage (cumulative) of release of atRA from saturated solutions of SiO$_{1000}$ and 1, 5 and 10% PDMS-atRA blends

| | Days Taken to Reach Percentage of Release | | | |
|---|---|---|---|---|
| Cumulative Percentage | SiO$_{1000}$ (412.5 µg/mL) | 1% Blend (651.0 µg/mL) | 5% Blend (699.8 µg/mL) | 10% Blend (812.7 µg/mL) |
| 70 | 8.2 | 15.2 | 12.8 | 16.4 |
| 80 | 14.0 | 30.9 | 21.9 | 48.2 |
| 90 | 35.0 | *121.9* | 75.1 | *153.1* |
| 100 | *110.6* | *214.9* | *144.9* | *251.5* |

Extrapolated values in italics

Release Studies Using Non-Saturation Concentrations of atRA Within SiO and Blends In the previous section it was observed that higher initial solubilised concentrations of atRA maintained the longest release profiles, however, the ability of the affinity of atRA to PDMS-atRA to slow the release rate was not shown conclusively. To investigate this further, a series of release experiments where varying but similar amounts of atRA were solubilised into SiO$_{1000}$ and blends with PDMS-atRA was carried out. The cumulative percentage release values are presented in Table 6. No noticeable release differences were observed between the SiO$_{1000}$ and the SiO$_{1000}$/PDMS-atRA blends, apart from when 10% PDMS-atRA was present within the blend. The time needed to release 80% of the atRA solubilised in SiO$_{1000}$ and the 1 and 5% blends is on average 16 days (2 weeks) whereas for the 10% blend, this increases to nearly 51 days (>three times longer, ~7 weeks).

TABLE 6

Number of days needed to reach a certain percentage (cumulative) of release of atRA from SiO$_{1000}$ and 1, 5 and 10% blends containing approximately the same initial amount of atRA, i.e. 50 µg/mL.

| | Days Taken to Reach Percentage of Release | | | |
|---|---|---|---|---|
| Cumulative Percentage | SiO$_{1000}$ (49.2 µg/mL) | 1% Blend (58.3 µg/mL) | 5% Blend (48.4 µg/mL) | 10% Blend (46.2 µg/mL) |
| 10 | <1 | <1 | <1 | <1 |
| 20 | <1 | 1 | <1 | <1 |

TABLE 6-continued

Number of days needed to reach a certain percentage (cumulative) of release of atRA from SiO$_{1000}$ and 1, 5 and 10% blends containing approximately the same initial amount of atRA, i.e. 50 µg/mL.

| | Days Taken to Reach Percentage of Release | | | |
|---|---|---|---|---|
| Cumulative Percentage | SiO$_{1000}$ (49.2 µg/mL) | 1% Blend (58.3 µg/mL) | 5% Blend (48.4 µg/mL) | 10% Blend (46.2 µg/mL) |
| 30 | 1.7 | 1.7 | 1.8 | 1.6 |
| 40 | 2.2 | 2.3 | 2.3 | 2.4 |
| 50 | 3.1 | 3.1 | 3.8 | 4.6 |
| 60 | 5.1 | 4.9 | 6.2 | 7.9 |
| 70 | 8.7 | 8.6 | 8.9 | 15.3 |
| 80 | 16.2 | 14.8 | 17.1 | 50.8 |
| 90 | 59.0 | 39.1 | 65.5 | *150.8* |
| 100 | *175.8* | *172.0* | *159.7* | *244.0* |

Extrapolated values in italics.

An underlying problem with the release observed for the desired time range (seven weeks) was that the initial burst release took the concentrations above the toxic range for the ARPE-19 cells ($10^{-4}$–$10^{-5}$ M). To ensure that the release period were definitely independent of the initial amounts of atRA, an experiment utilising varying amounts of atRA in SiO$_{1000}$ (ranging from 13.2 to 412.5 µg/mL) was carried out. From this it was determined that the release period was independent of atRA starting concentration.

After determining that the release rates were independent of atRA starting concentration in SiO$_{1000}$, the impact of the presence of PDMS-atRA blends was also studied. When the release from saturated blends was compared with the release from a blend with an approximate starting concentration of 50 µg/mL, it appeared that the amount of PDMS-atRA present in the blend controlled the release time as shown in Table 7. If we compare SiO$_{1000}$ with a SiO$_{1000}$ blend with PDMS-atRA (10 vol %), 80% of the atRA initially present within SiO$_{1000}$ containing 40 or 400 µg/mL was released in 10 and 14 days respectively, whereas 80% of the atRA within a SiO$_{1000}$/PDMS-atRA 10% blend containing either 45 or 800 µg/mL was released in 51 and 48 days respectively. This suggests that the presence of the blends may extend the release period into the 6 week period that is required clinically.

TABLE 7

Table to show time (days) taken to reach certain percentages of cumulative release of atRA from solutions of SiO$_{1000}$, 5 and 10% blends of PDMS-atRA in SiO$_{1000}$ (v/v) with various initial concentration of atRA.

| | Days Taken to Reach Percentage of Release | | | | | |
|---|---|---|---|---|---|---|
| Cumulative Percentage | SiO$_{1000}$ 49.3 µg/mL | SiO$_{1000}$ 412.5 µg/mL | 5% Blend 48.4 µg/mL | 5% Blend 699.8 µg/mL | 10% Blend 46.2 µg/mL | 10% Blend 813 µg/mL |
| 10 | <1 | <1 | <1 | 1.1 | <1 | 1.2 |
| 20 | <1 | <1 | <1 | 1.8 | <1 | 1.8 |
| 30 | 1.8 | 1.6 | 1.8 | 2.9 | 1.6 | 3.1 |
| 40 | 2.3 | 2.4 | 2.3 | 4.1 | 2.4 | 4.2 |
| 50 | 3.1 | 3.3 | 3.8 | 6.8 | 4.6 | 7.2 |
| 60 | 5.1 | 5.4 | 6.2 | 9.2 | 7.9 | 9.9 |
| 70 | 8.7 | 8.2 | 8.9 | 12.8 | 15.3 | 16.4 |
| 80 | 16.2 | 14.0 | 17.1 | 21.9 | 50.8 | 48.2 |
| 90 | 59.0 | 35.0 | 65.5 | 75.1 | *150.8* | *153.1* |
| 100 | *171.0* | *110.6* | *159.7* | *144.9* | *244.0* | *251.5* |

Extrapolated values in italics.

This is an exciting prospect as the potential to tailor the initial starting concentration to avoid the toxicity of the burst release ARPE-19 cells and maintain the sustained release amounts above the therapeutic level for an anti-proliferative effect may be achievable.

atRA Release from $SiO_{5000}$:$SiO_{1000}$ Blends

Whilst some surgeons prefer using $SiO_{1000}$ as a tamponade agent, some prefer to use $SiO_{5000}$. Due to $SiO_{5000}$ having a higher viscosity, it reduces the risk of emulsion formation within the eye after administration. A preliminary comparative experiment was carried out in which the release profile of atRA from a $SiO_{1000}$ solution was evaluated against the release from a 50/50 $SiO_{1000}$/$SiO_{5000}$ solution. To achieve the same starting concentration of atRA in both of the oils, a solution of atRA in $SiO_{1000}$ was prepared, stirred for 2 weeks and filtered following the same protocol as described previously. Once filtered, the solution was divided into two vials and the appropriate volume of $SiO_{5000}$ was added to one to create a 50/50 blend of $SiO_{1000}$/$SiO_{5000}$, while the second one was diluted with $SiO_{1000}$. The resulting oils had an initial concentration of 32 µg/mL of atRA.

Figure 7:
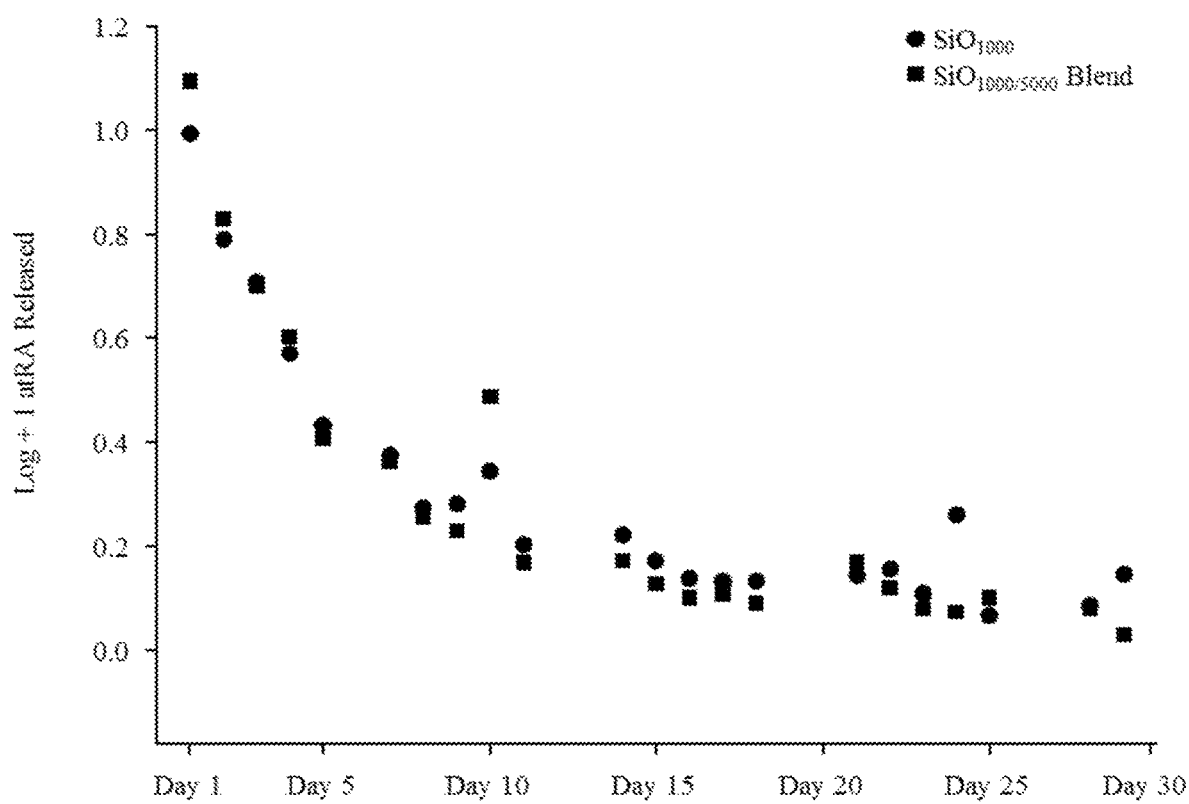
FIG. 7 shows release of atRA (starting concentration 32 μg/mL) from $SiO_{1000}$ and $SiO_{1000/5000}$ blend into culture media presented on a log+1 scale.

Release of atRA (starting concentration 32 µg/mL) from $SiO_{1000}$ (●) and $SiO_{1000/5000}$ blend (■) into culture media presented on a log+1 scale is shown in FIG. 7. Experiments were carried out at 37° C. in a 5% $CO_2$ atmosphere.

FIG. 7 shows there is no apparent difference in atRA release from either $SiO_{1000}$ or a $SiO_{1000/5000}$ 50/50 vol % blend. It appears, therefore, that the viscosity of the oil does not seem to affect atRA release.

The invention claimed is:

1. A liquid ophthalmic tamponade composition comprising:
   i) a base oil comprising a silicone oil;
   ii) a free drug; and
   iii) an additive comprising a first segment that facilitates or modulates solubility in the base oil, conjugated to a second segment that facilitates or modulates solubility and/or release of the free drug, wherein the first segment comprises poly(dimethylsiloxane), the second segment comprises a group that aids solubility of the free drug in the base oil and/or modifies release of the free drug therefrom, wherein the second segment of the additive comprises a hydrophobic moiety comprising a group selected from $C_{1-25}$ alkyl groups, $C_{2-25}$ alkenyl groups, $C_{7-25}$ alkyl-aryl groups, $C_{8-25}$ alkenyl-aryl groups, $C_{1-10}$ alkyl-O-$C_{1-10}$ alkyl groups, amine groups, amide groups, or ester groups; and
   wherein the composition comprises of components that are suitable for application into the vitreous space of an eye.

2. The composition of claim 1, wherein the base oil further comprises one or more of a different silicone oil, a fluorinated silicone oil, or a perfluorocarbon oil.

3. The composition of claim 1, wherein the silicone oil is poly(dimethylsiloxane).

4. The composition of claim 1, wherein the base oil has a kinematic viscosity of from about 100 to about 10,000 cSt, from about 1,000 to about 5,000 cSt, or from about 1,000 to about 2,000 cSt.

5. The composition of claim 1, wherein the second segment of the additive comprises a moiety which is a drug molecule used in the eye.

6. The composition of claim 1, wherein the second segment of the additive comprises a moiety which is selected from anti-proliferative agents or derivatives thereof.

7. The composition of claim 6, wherein the anti-proliferative agents are selected from all-trans retinoic acid, derivatives of all-trans retinoic acid, or other derivatives of vitamin A.

8. The ophthalmic composition of claim 1, wherein the second segment of the additive comprises a moiety which is an anti-inflammatory agent or derivative thereof.

9. The composition of claim 1, wherein the free drug is selected from an anti-inflammatory drug, an anti-proliferative, an anti-oxidant drug, an anti-neoplastic drug, an anti-growth factor, or mixtures thereof.

10. The composition of claim 9, wherein the free drug is selected from all-trans retinoic acid and non-steroidal anti-inflammatories.

11. The composition of claim 1, wherein the free drug is present in an amount of from about 1 to about 1000 µg per ml; or from about 5 to about 900 µg per ml; or from about 10 to about 800 µg per ml; or from about 15 to about 700 µg per ml.

12. The composition as claimed in claim 1, wherein the segments of the additive are conjugated together via a group selected from an ester group, an amide group, a carbamate group, a carbonate group, an anhydride group, an imine group or an ether group.

13. The composition as claimed in claim 12 wherein the additive comprises one segment that facilitates or modulates solubility in the base oil, and two segments that facilitate or modulate free drug solubility and/or free drug release, wherein the segments that facilitate or modulate free drug solubility and/or free drug release are conjugated to opposite sides of the segment that facilitates or modulates solubility in the base oil, via two groups, which are the same or different.

14. The composition as claimed in claim 12, wherein the conjugating group is an ester group.

15. The ophthalmic composition of claim 8, wherein the anti-inflammatory agent is selected from ibuprofen, derivatives of ibuprofen, or derivatives of other non-steroidal anti-inflammatory agents.

16. A method of treating or ameliorating an eye disorder comprising administering an effective amount of a composition as claimed in claim 2 to a patient in need thereof.

17. The method of treating or ameliorating an eye disorder according to claim 16, wherein the eye disorder is a proliferative retinal pigment epithelium disease, a detached retina, a torn retina, proliferative vitreoretinopathy, retinal pigment epithelium cell proliferation, or other disease, condition or disorder associated with an abnormality in the retinal pigment epithelium or its function.

* * * * *